United States Patent [19]

Petrofsky

[11] Patent Number: 4,558,704
[45] Date of Patent: Dec. 17, 1985

[54] HAND CONTROL SYSTEM

[75] Inventor: Jerrold S. Petrofsky, Beavercreek, Ohio

[73] Assignee: Wright State University, Dayton, Ohio

[21] Appl. No.: 561,720

[22] Filed: Dec. 15, 1983

[51] Int. Cl.[4] .............................................. A61N 1/08
[52] U.S. Cl. ................................................ 128/423 R
[58] Field of Search .............. 3/1, 1.1; 128/77, 419 R, 128/421-423, 733

[56] References Cited

U.S. PATENT DOCUMENTS

| | | | |
|---|---|---|---|
| 3,083,712 | 4/1963 | Keegan | 128/423 R |
| 3,344,792 | 10/1967 | Offner et al. | 128/142 |
| 3,364,929 | 1/1968 | Ide et al. | 128/172.1 |
| 3,449,769 | 6/1969 | Mizen | 623/26 |
| 3,929,335 | 12/1975 | Malick | 272/57 R |
| 4,030,141 | 6/1977 | Graupe | 3/1.1 |
| 4,157,087 | 6/1979 | Miller et al. | 128/423 R |
| 4,165,750 | 8/1979 | Aleev et al. | 128/422 |
| 4,236,528 | 12/1980 | Stanec et al. | 128/782 |
| 4,260,035 | 4/1981 | Loveless et al. | 180/6.5 |
| 4,314,379 | 2/1982 | Tanie et al. | 3/1.1 |
| 4,381,012 | 4/1983 | Russek | 128/644 |
| 4,421,336 | 12/1983 | Petrofsky et al. | 280/252 |
| 4,480,830 | 11/1984 | Petrofsky et al. | 128/423 W |
| 4,499,900 | 2/1985 | Petrofsky et al. | 128/423 |

FOREIGN PATENT DOCUMENTS 3030897  3/1982  Fed. Rep. of Germany .

OTHER PUBLICATIONS

Restoration of Hand Function in the Quadriplegic Through Electrical Stimulation by P. Hunter Peckham & J. Thomas Mortimer, Published in Book entitled "Functional Electrical Stimulation," edited by Hambrecht and Reswick-Marcel Dekker, Inc. pp. 83-9-5-1977.
Article by Patrick E. Crago et al., entitled "Closed-Loop Control of Force During Electrical Stimulation of Muscle"-Published in IEEE Transactions on Biomedical Engineering, vol. BME-27, No. 6, Jun. 1980, pp. 306-312.
Functional Neuromuscular Stimulation-Third Progress Report, Apr. 1981 & Fourth Progress Report, Jul. 1981, Prepared for the National Institutes of Health.
Functional Neuromuscular Stimulation-Eighth Progress Report, Jul. 27, 1982, Prepared for the National Institutes of Health.
Scott et al., "Sensory Feedback System Compatible with Myoelectric Control" Med. & Biol. Eng. & Comput. Jan. 1980, vol. 18, pp. 65-69.
Shannon "A Myoelectrically Controlled Prosthesis with Sensory Feedback" Med. & Biol. Eng. & Comput. Jan. 1979, vol. 17, pp. 73-80.
Rakic "An Automated Hand Prosthesis" Med Electron Biol Engng Mar. 1964, vol. 2, No. 1, pp. 47-55.

Primary Examiner—William E. Kamm
Assistant Examiner—Mitchell J. Shein
Attorney, Agent, or Firm—Biebel, French & Nauman

[57] ABSTRACT

A system for stimulating a grasping action by a paralyzed hand. The system includes a sensor arrangement for detecting movement of a shoulder by the paralyzed person. The sensor transmits shoulder movement signals to a computerized controller which generates stimulation signals for stimulation electrodes mounted within a cuff worn about the forearm which supports the hand to be stimulated. Closed loop control is accomplished by use of a glove to which are attached a length sensor and a pressure sensor connected for alternative selection. Stimulation of deeply buried muscles is accomplished by arranging the stimulation electrodes into side-by-side electrode sets which are so positioned as to produce focusing of stimulation energy at the location of the subject muscle.

26 Claims, 15 Drawing Figures

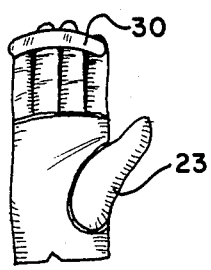
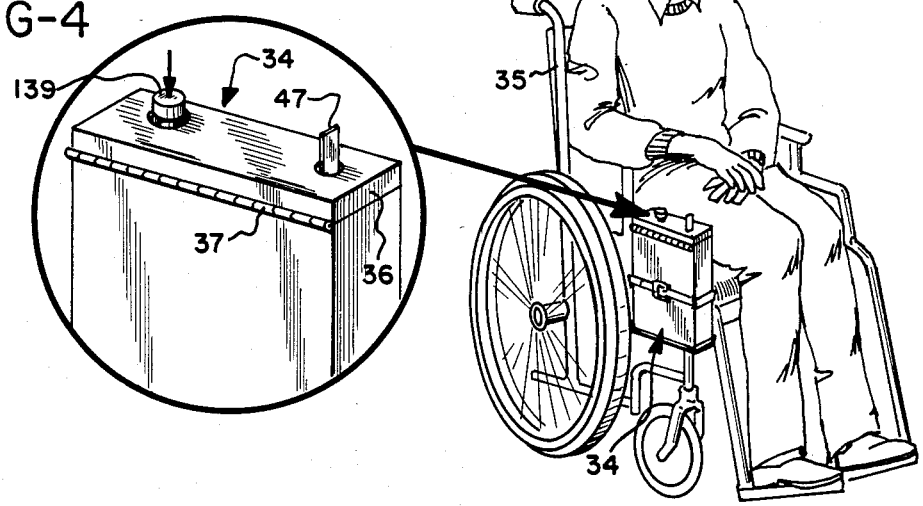
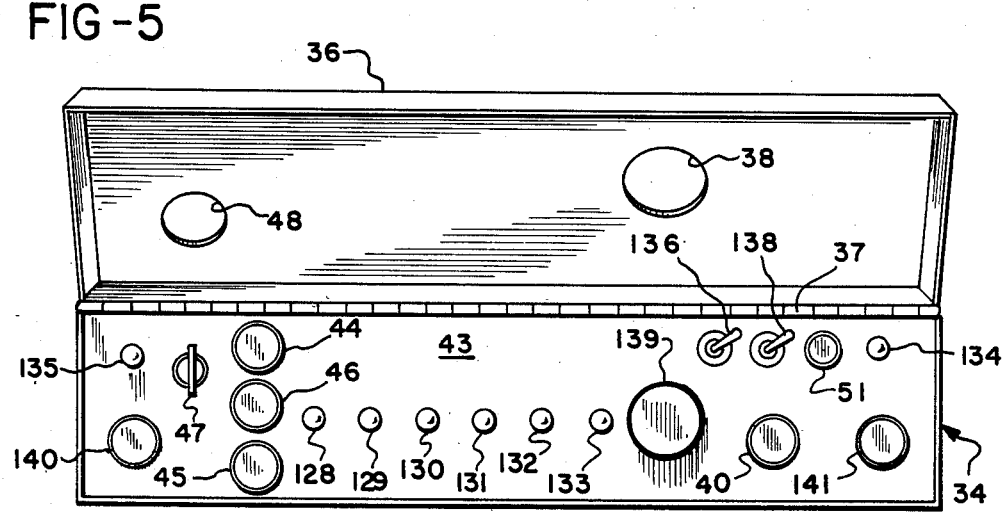

FIG-6
FIG-6a
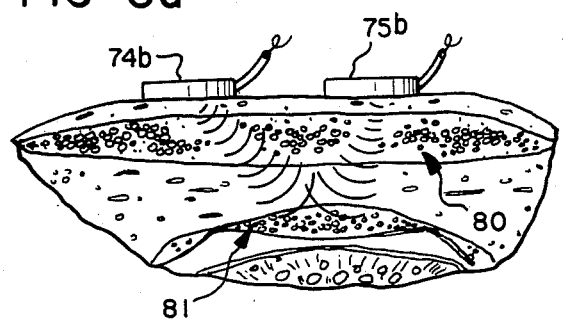
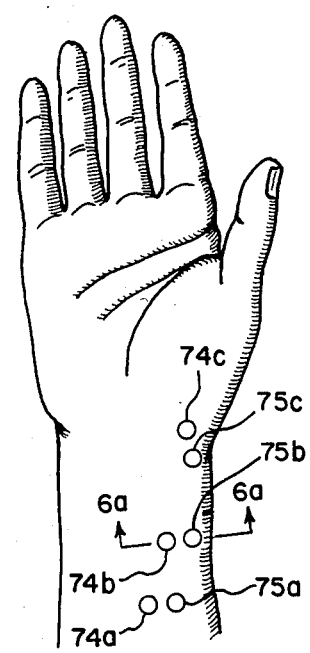
FIG-7
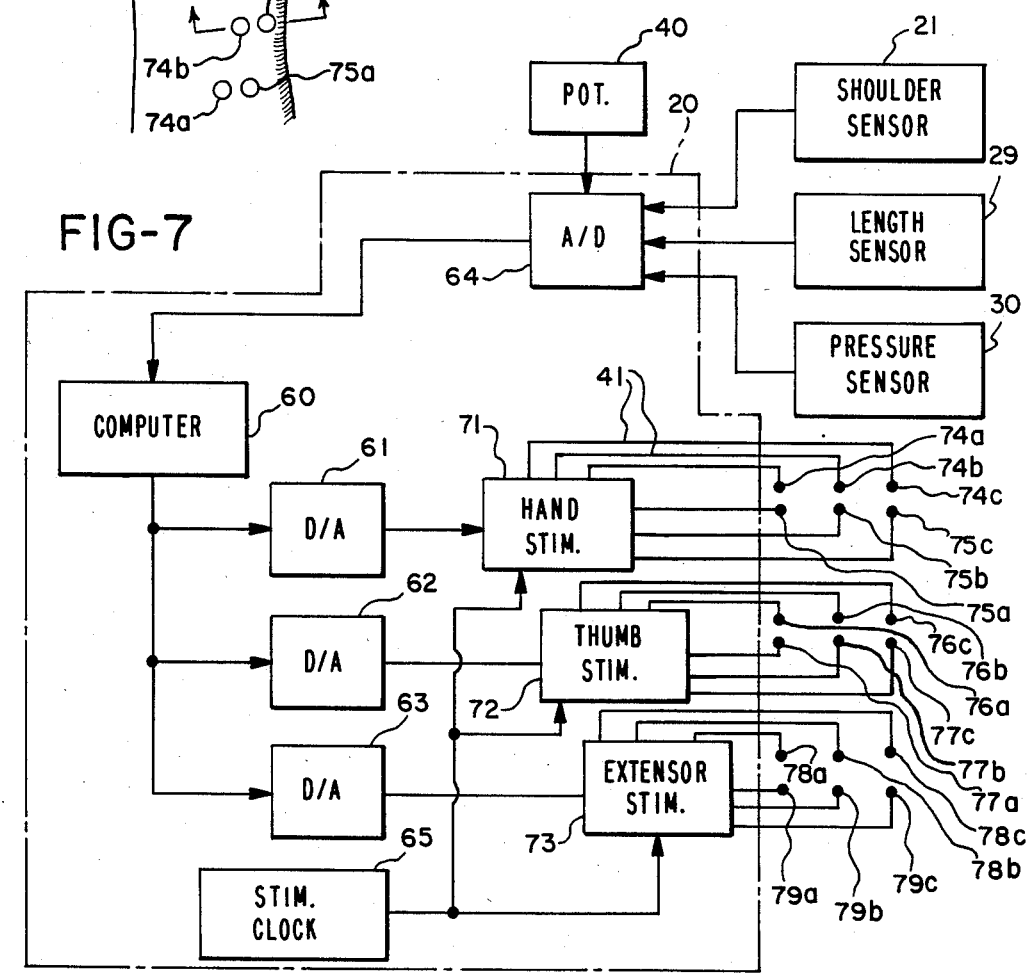

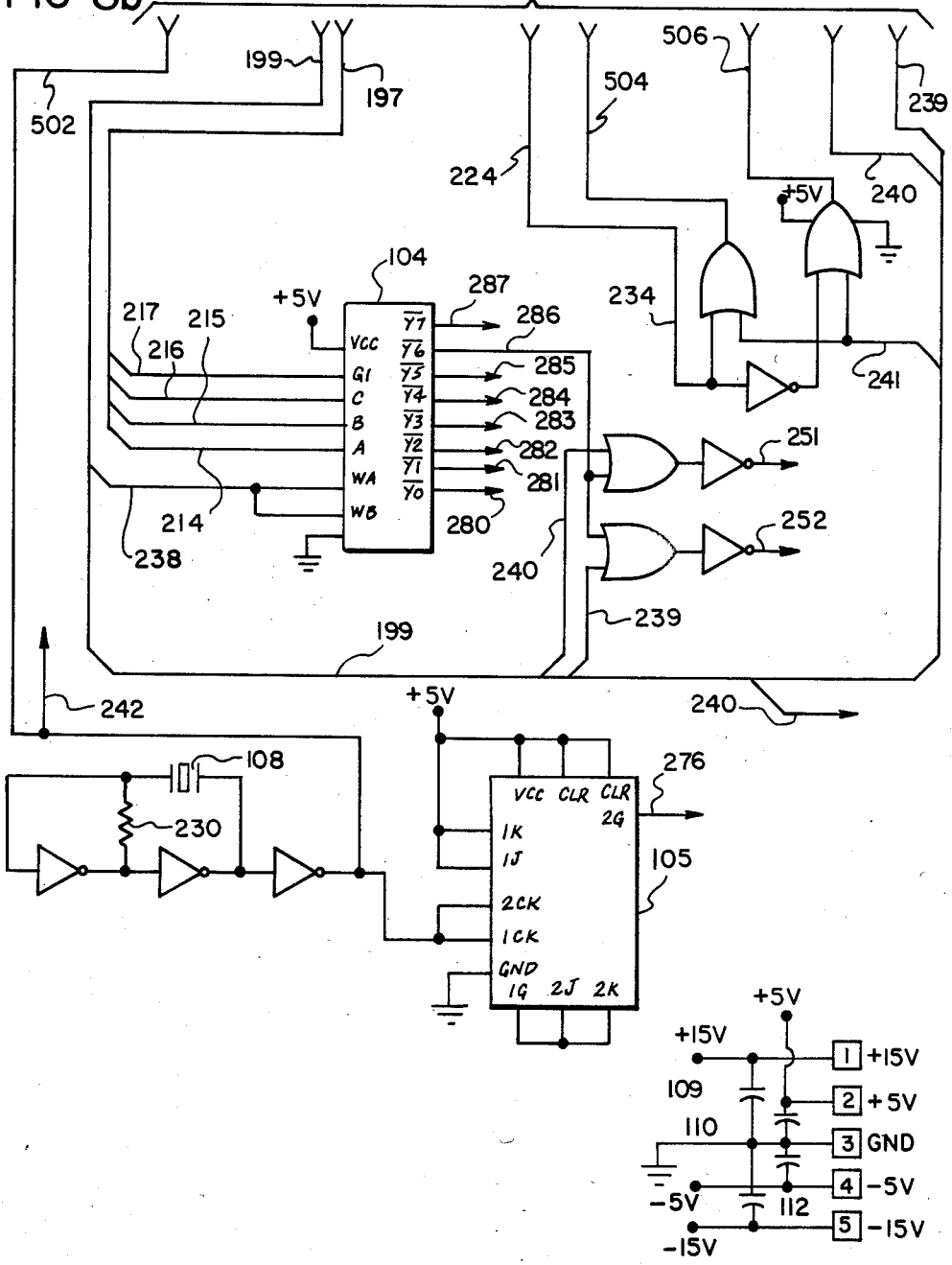

HAND CONTROL SYSTEM

BACKGROUND OF THE INVENTION

This invention relates to muscle stimulation systems for paralyzed persons. More particularly, this invention relates to a stimulation system for producing a grasping action by a paralyzed hand.

Typical prior art devices for stimulating paralyzed muscles are described in Petrofsky et al U.S. application Ser. No. 444,647, filed Nov. 26, 1982 and in other references cited therein. These prior art systems have a set of three electrodes for each muscle group to be stimulated. The electrodes are placed on the surface of the skin above the muscle group to be stimulated and are excited by pairs of pulsed stimulation signals. One of the three electrodes is connected to a high voltage ground, and voltage pulses are applied between that electrode and the other two electrodes in alternating fashion. The series of pulses applied between the ground electrode and one of the active electrodes occur at a frequency of about 60 Hz, and these pulses are alternated with 60 Hz pulses applied between the ground electrode and the other active electrode. The pulse width is disclosed as being about 500 microseconds, and the pulse amplitude varies in accordance with the desired stimulation level up to a maximum of about 255 volts. Such stimulation produces recruitment of all motor units and results in maximum effort by the muscle. Feedback signals are provided in order to control the amplitude of the applied stimulation signals in an automatic manner.

The above-described stimulation technique has been used heretofore only for stimulation of leg muscles. Leg muscles have been so stimulated for operation of exercise equipment, for pedaling vehicles and for walking. Prior to this invention no attempt has been made to apply such techniques to arm or hand muscles. The present invention enables stimulation of the hand of a quadriplegic person to grasp and hold an object such as a drinking glass, a comb, a toothbrush or a fork.

Quadriplegic persons often times owe their condition to some type of accident which has produced spinal cord injury. If the injury occurs farther down on a spinal cord, only the legs are paralyzed, and a paraplegic condition results. Injuries at a higher point in the spinal cord produce various degrees of immobilization of the arms and hands. It sometimes happens that the arms and shoulders can be moved and that the hands while paralyzed, have retained the sense of touch. In other cases there is no sense of touch in the hands. This invention relates to both of the above-mentioned types of quadriplegia.

SUMMARY OF THE INVENTION

In accordance with this invention there is provided a hand control system for helping quadriplegics to gain greater independence by assisting them in such daily personal chores as combing hair, brushing teeth and using eating utensils. The system is designed to utilize open loop control techniques or closed loop control techniques, depending upon the needs of the particular individual. The system utilizes stimulation electrodes which are placed on the surface of the skin above the forearm to activate the hand flexors, the thumb flexors and the wrist extensors.

Closing and opening of the hand is activated by movement of the opposite shoulder. A linear potentiometer is mounted on the shoulder so as to generate an electrical signal corresponding to the amount of shoulder movement. An analog to digital converter receives the output signal from the linear potentiometer and transmits a digital representation thereof to a portable digital computer. The computer processes the shoulder movement signal and generates digitized control signals for the above-mentioned muscles. These control signals are converted to analog form and applied to stimulators of appropriate design.

As thus far described the system is open loop in nature in that the quadriplegic person exercises total control of hand movement through shoulder movement alone. This requires eye-shoulder coordination and some sense of feeling in the hand. The stimulation signals are applied by electrodes mounted within a tailor made cuff worn about the forearm of the quadriplegic person.

For persons who have no feeling in their hands a special glove is provided. The glove is provided with a length sensor and a pressure sensor which provide feedback signals for closed loop control. The feedback signals are digitized and compared with reference signals provided by the shoulder sensor. The resulting error signals are used for appropriate adjustment of the stimulation driving signals. Thus the shoulder provides pressure or length control signals during closed loop control, as opposed to the position signals generated during open loop operation.

Proper operation of the system requires calibration of the shoulder-mounted potentiometer in order to establish a zero position. In the open loop mode there is no movement of the hand when the shoulder is at the zero position. If the shoulder is moved back from this position the hand opens. If it is moved in the forward direction the hand will close. The greater the forward movement the greater the hand closure. In the closed loop mode shoulder movement produces a similar hand opening and closing response. However, stimulation voltage is increased only until the desired pressure, the desired length of stretch or a maximum stimulation voltage is reached. In all modes the computer regularly performs a test to determine whether or not the shoulder mounted potentiometer is firmly in place. For this purpose the above-mentioned potentiometer is mounted to the shoulder and chest by a pair of ECG electrodes, across which a low current, high frequency electrical signal is placed. The current is broken if either of the electrodes breaks loose from the skin, and this is sensed by the computer.

It is therefore an object of this invention to provide apparatus and method for stimulating movement of the hand of a human being by sensing a voluntary body movement and generating hand stimulating signals in response to the movement, so sensed.

Other objects and advantages of the present invention will be apparent from the following description, the accompanying drawings, and the appended claims.

BRIEF DESCRIPTION OF THE DRAWINGS

FIG. 3 is an illustration of a glove with a pressure sensor mounted thereon;

FIG. 4 illustrates a hand control system mounted on a wheelchair;

FIG. 5 is a pictorial drawing of a control panel for a hand control system;

FIG. 6 is an illustration of a human hand showing typical mounting locations for a set of stimulation electrodes which control flexing of the flexor digitorum profundus manus muscle group;

FIG. 6a is an enlarged cross section taken along lines 6a—6a of FIG. 6;

FIG. 7 is a schematic block diagram of a hand control system;

FIGS. 8a and 8b are a schematic diagram of a portion of a computer for a hand control system;

DESCRIPTION OF THE PREFERRED EMBODIMENT

Figure 1:
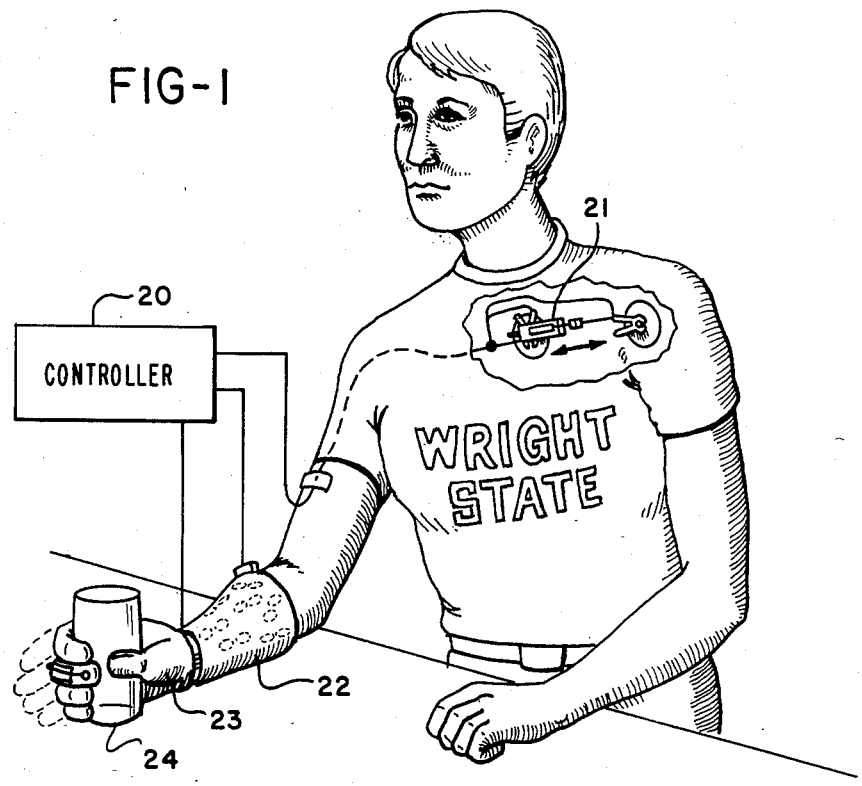
FIG. 1 is a schematic illustration of a hand control system mounted on the body of a quadriplegic person.

FIG. 1 illustrates a hand control system in accordance with the present invention as mounted on the body of a quadriplegic person. As illustrated therein, the system comprises shoulder sensor 21, a controller 20, a cuff 22 and a glove 23. Under control of the system the hand of the quadriplegic person may be stimulated to grasp an object such as a glass 24.

Figure 2:
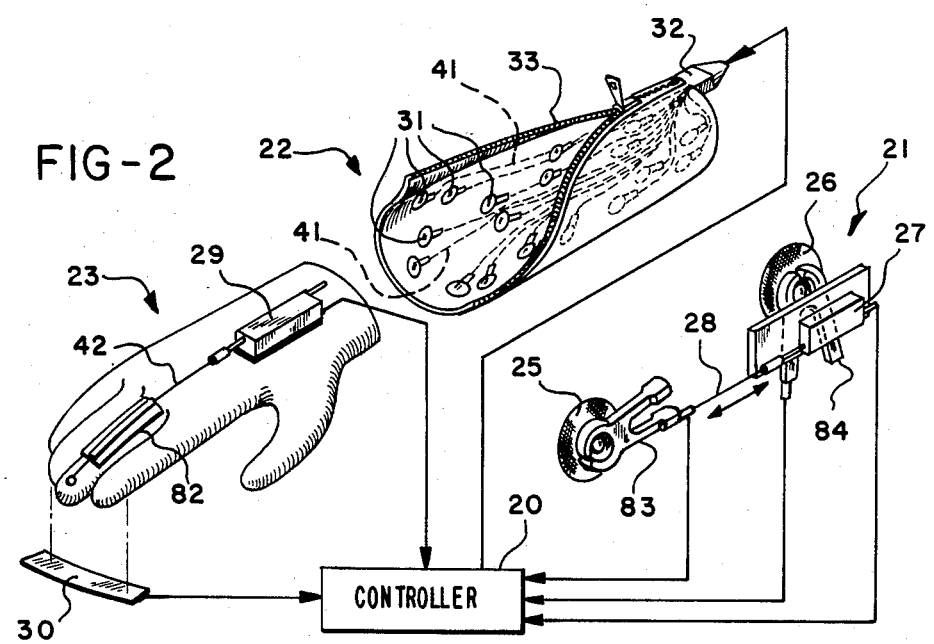
FIG. 2 is an enlarged view of the apparatus generally illustrated in FIG. 1.

As shown in more detail in FIG. 2, shoulder sensor 21 comprises a linear potentiometer connected to a sliding wire 28. Potentiometer 27 may be a device of the type sold by Bourns, Inc. under Part No. 2051414101. Potentiometer 27 is supported by a clip 84 attached to an ECG electrode 26. Electrode 26 may be a prejelled self-adhering disposable electrode of the type sold by NDM Corporation of Dayton, Ohio under Catalog No. 01-3330. Electrode 26 is adhered to the skin of the quadriplegic person opposite another similar electrode 25. There is a clip 83 attached to electrode 25 for supporting the end of the sliding wire 28. It will be seen that one of electrodes 25, 26 is attached to the shoulder of the quadriplegic person, while the other electrode is attached to the chest. Thus when the shoulder is flexed relative to the chest a sliding motion of wire 28 is produced. This causes movement of a pick-off across resistor within potentiometer 27, thereby generating a variable voltage output for sensing by controller 20.

Figure 12:
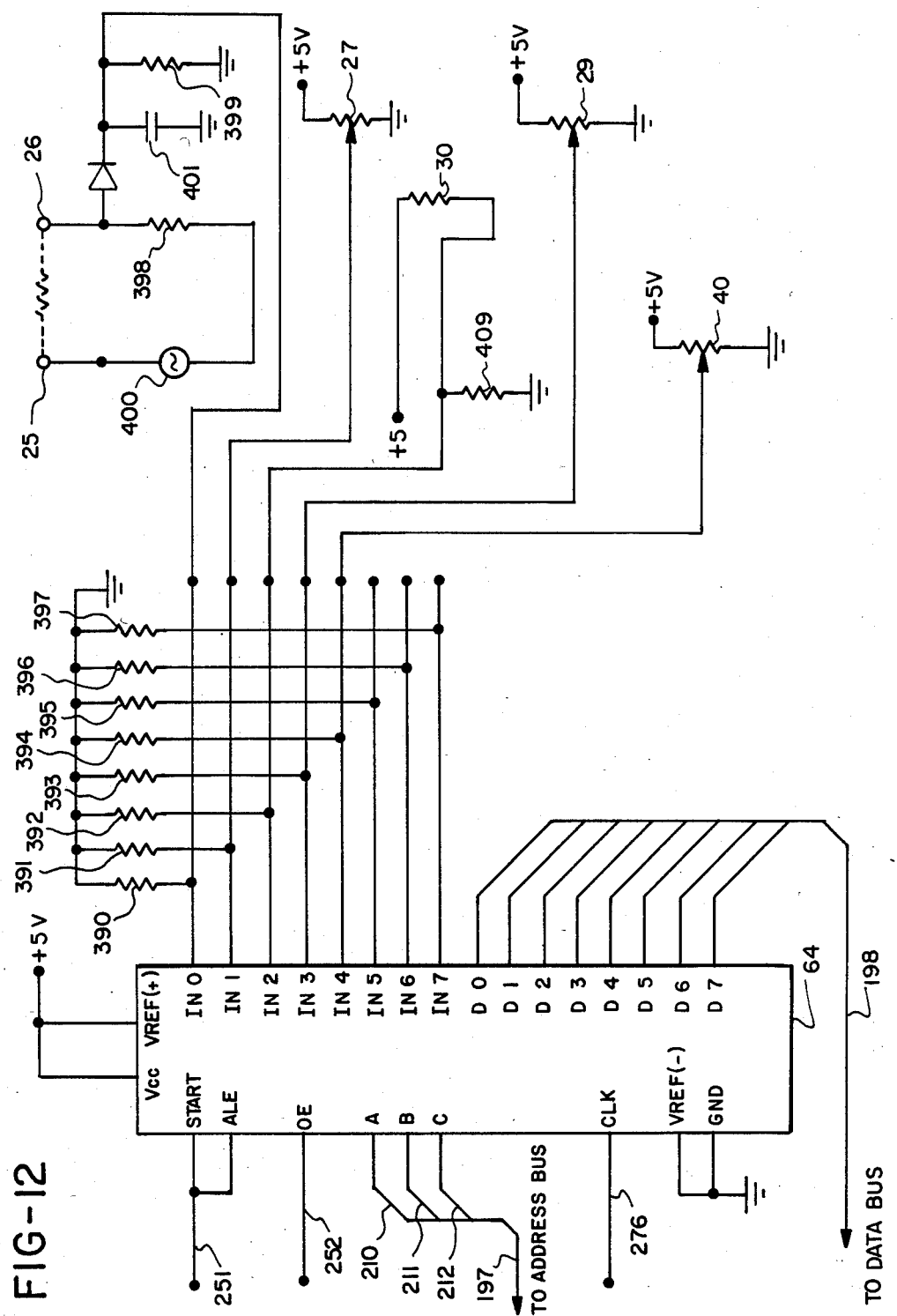
FIG. 12 is a schematic diagram of interconnections between hand control feedback sensors and an analog to digital converter.

Controller 20 includes a ten KHz oscillator 400, as illustrated in FIG. 12. Oscillator 400 may be a Signetics SE/NE 555 timer connected as shown in the manufacturer's data sheets for generation of a free running frequency of 10 KHz. When electrodes 25 and 26 are firmly adhered to the skin of the quadriplegic person, then a current of approximately one milliampere is delivered by oscillator 400 through a resistor 398 and across the skin bridging the two electrodes. This current flow creates a potential drop which is sensed by controller 20. If either of electrodes 25 or 26 breaks loose from the skin (approximately 5000 ohms) of the wearer, then a potential change is signaled to controller 20. This results in generation of an error signal which terminates the stimulation of the hand.

Continuing with the description of FIG. 2, cuff 22 comprises a series of electrodes 31, each attached to a lead wire 41 woven into the fabric of the cuff. Lead wires 41 extend toward a connector 32 mating with another connector (not illustrated) for connection to controller 20. Cuff 22 may comprise 18 electrodes 31 arranged in three groups of six electrodes each. One group of electrodes stimulates the hand flexors, another group stimulates the thumb flexors and the third stimulates the wrist extensors. The precise placement for the electrodes must be tailored to fit the particular individual. Thus the fabrication of cuff 22 must be preceded by a fitting procedure wherein electrodes are placed on the skin of the subject above the muscles to be stimulated and then moved slightly back and forth for production of maximum stimulation effect. Reference may be made to FIG. 6 for the approximate locations of a group of electrodes for stimulating the hand flexors. Once the optimum locations have been identified, a pattern is made from which cuff 22 is produced.

Electrodes 31 may be MEDTRONIC Model 3795 electrodes sold by Medtronic, Inc. of Minneapolis, Minn. A zipper 33 secures cuff 22 firmly about the forearm of the wearer, thereby assuring that electrodes 31 are accurately secured in place. A small tattoo may be placed on the arm of the quadriplegic person for use in aligning the cuff.

Glove 23 includes a length sensing arrangement and a pressure sensor for providing feedback signals to controller 20. If the quadriplegic person has any feeling in his hand, then glove 23 is not required. In that case the person's sensory system provides the required feedback to indicate when a proper degree of grasping pressure has been stimulated. At that point the shoulder postion is maintained. Thereafter, the hand is opened by backward movement of the shoulder. It will be noted that the shoulder which operates the stimulation system is that shoulder which is opposite the hand being stimulated.

For quadriplegics who do not have any feeling in their hands, glove 23 provides a most useful function. In one mode of operation glove 23 provides a closure feedback signal generated by a length sensing arrangement comprising linear pontentiometer 29, a sliding wire 42 and a piece of adhesive tape 82 for securing wire 42 in place. As the hand closes into a grasping posture under control of the stimulation system, the wire 42 is extended thereby causing generation of a corresponding output potential from the potentiometer 29. Potentiometer 29 may be a linear potentiometer of the same type as potentiometer 27. Alternatively, the illustrated length sensing arrangement may be replaced by a simple strip of carbon elastomer material available from the University of Glasgow, Glasgow, Scotland. This material readily elongates to accommodate the closure of the hand which is wearing the glove. As the material stretches, its electrical resistance changes, and this is easily sensed by a simple resistance measuring circuit.

Pressure sensor 30 may be utilized for providing a feedback signal as an alternative to the above-mentioned length sensing arrangement. Pressure sensor 30 preferably is a carbon elastomer material of the type described above. A strip of such material may be secured to glove 23 as best illustrated in FIG. 3. Alternatively, pressure sensor 30 may comprise a piezoelectric crystal or other known arrangement for pressure sensing applications.

Controller 20 may be mounted within a portable box 34 which may be fastened to a wheelchair 35 as illustrated in FIG. 4. Box 35 may be equipped with a cover 36 secured thereto by a hinge 37. Cover 36 is provided with a pair of apertures 38 and 48 as best illustrated in FIG. 5. A reset button 139 and a stimulator power switch 48 are mounted on a control panel 43 for extending through apertures 38 and 48 respectively when the cover 36 is closed. The various switches on control panel 43 are set up once daily for programming controller 20. Thereafter, cover 36 is closed, and the quadriplegic person may engage in a day's activities utilizing the system. Reset button 139 permits immediate termination of muscle stimulation as desired by the user for any reason. Stimulator power switch 47 is provided for shutting off power to the stimulator circuits without powering down the computer portion of controller 20. This enables power conservation during relatively long periods of inactivity without requiring reprogramming of the computer.

Control panel 43 also includes a main power switch 51, which controls all power to the system, a pair of feedback designation switches 136 and 138, control knobs for four potentiometers 40, 44, 45 and 46 and a pair of programming pushbuttons 140 and 141. During the daily programming routine potentiometers 44, 45 and 46 are adjusted to produce threshold stimulation of the hand flexors, thumb flexors and wrist extensors respectively when a predetermined calibration signal is generated by the computer. Also during the programming routine potentiometer 40 is adjusted for limiting the maximum stimulation voltage to that value which just begins to produce physical discomfort. One or the other of switches 136 or 138 may be thrown to designate a feedback routine. Switch 136 selects pressure feedback while switch 138 selects length feedback.

Control panel 43 additionally includes eight light emitting diodes 128 through 134. The diodes light up to lead the user through a programming routine. LED 128 indicates that power is on and that the system is inactive. LED 129 calls for adjustment of potentiometers 44 through 46 to set the simulation threshold, while LED 130 directs the user to adjust potentiometer 40 for setting the maximum stimulation voltage. LED 131 signals that it is time for shoulder movement to adjust the zero setting. LED 132 indicates that power is on, and LED 133 indicates that the system is programmed and active.

All controls on control panel 43 are designed for manipulation by a quadriplegic person. Following each control setting during the programming sequence one or the other of push buttons 140 or 141 must be depressed. The correct push buttons are indicated by LEDs 135 and 134 respectively. The system provides two such pushbuttons at opposite ends of the control panel to accommodate the lack of dexterity of a quadraplegic person. Activation of the push buttons alternates from left to right.

Figure 13:
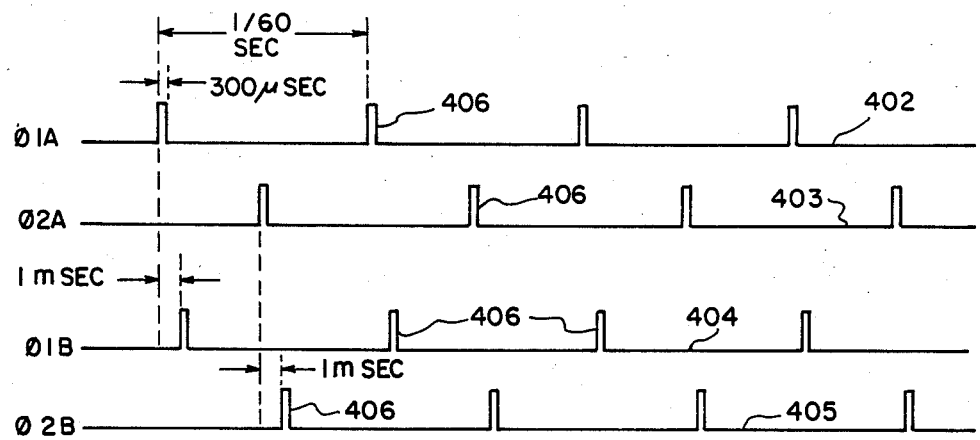
FIG. 13 is a timing diagram for four stimulation signals.

Referring now to FIG. 6, a typical placement of a group of six stimulating electrodes will be observed. The group comprises a first set of three electrodes, designated 74a through 74c and a second set designated 75a through 75c. All six electrodes of the general type designated by the reference numeral 31 of FIG. 2. Electrodes 74a, 74b and 74c are excited by a series of alternating pulses of electrical energy generated in the manner described in Petrofsky et al U.S. application Ser. No. 417,934, filed Sept. 14, 1982. Accordingly, electrode 74c is connected to a high voltage ground while electrodes 74a and 74b are connected to pulsed sources of electrical potential. In a typical operation pulses are applied in alternating fashion, first across the electrode pair 74a–74c and then across the electrode pair 74b–74c. These alternating pulses are each applied at a frequency of about 60 Hz, and the pulses are of about 300 microseconds duration, all as taught in the Petrofsky et al application. The circuitry as hereinafter described in detail supplements the prior art electrode arrangement by adding a second set of three electrodes for cooperative excitation. Thus electrode 75c is connected to a high voltage ground while electrodes 75a and 75b are connected to sources of pulsed potential. The driving circuitry for electrodes 75a through 75c is identical to the driving circuitry for electrodes 74a through 74c. The operation of those circuits is likewise identical except for the fact that there is a phase shift between the two pairs of signals. The circuitry as hereinafter described provides a phase delay which may be adjusted anywhere in the range between about 100 microseconds and slightly over one millisecond, but a delay of about one millisecond is preferred. FIG. 13 illustrates waveforms for the signals which result.

FIG. 13 illustrates four waveforms 402 through 405 generated in response to stimulation clock signals hereinafter referred to as $\phi_{1A}$, $\phi_{2A}$, $\phi_{1B}$ and $\phi_{2B}$ respectively. The signal illustrated by waveforms 402 is applied across the electrode pair 74a–74c while the signal represented by the waveforms 403 appears across the electrode pair 74b–74c. Each waveforms comprises a series of 300 microsecond pulses 406 generated at a frequency of about 60 Hz. The pulses in waveforms 402 and 403 are alternated, as taught by the prior art.

Waveforms 404 and 405 represent stimulation signals occurring across electrode pairs 75a–75c and 75b–75c respectively. Waveforms 404 and 405 are identical to waveforms 402 and 403 that are shifted relative thereto so as to have a phase delay preferably in the amount of about one millisecond.

FIG. 6a is a cross section across the forearm of a quadriplegic person taken along lines 6a—6a of FIG. 6. The figure illustrates two electrodes 74b and 75b placed on the surface of the skin just above a mass of muscular tissue which may be the flexor digitorum sublimis and flexor digitorum superficialis manus muscle groups as represented by the reference numeral 80. Below those muscle groups lies the flexor digitorum profundus manus muscle group represented by the reference numeral 81. The latter muscle group controls hand flexure. The hand control system as described herein stimulates the flexor digitorum profundus manus muscle group without stimulating the muscle groups thereabove. The side-by-side placement of electrode groups having phase displaced signals applied thereto is believed to provide a focusing effect which is sensed by the deep muscles but not by the superficial muscles. This effect is enhanced by adjusting the stimulation voltage levels somewhat downwardly to a point where a single electrode set such as the set 74a through 74c is unable to stimulate the superficial muscles.

FIG. 7 presents a block diagram of the entire hand control system. That figure illustrates the six above-described electrode terminals 74a through 74c and 75a through 75c connected by lead lines 41 to a hand stimulating circuit 71. Similarly, a second group of six electrodes 76a through 76c and 77a through 77c are connected to a thumb stimulating circuit 72, while a third group of six electrodes 78a through 78c and 79a through 79c are connected to an extensor stimulating circuit 73. Electrodes 76a through 76c and 77a through 77c stimulate thumb flexing by stimulation of the relatively deep adductor pollicis muscle group without stimulation of superficial muscles thereabove. Electrodes 78a through 78c and 79a through 79c produce opening of the hand by stimulation of the extensor carpi ulnaris muscle group. This is also a relatively deep muscle group which must be stimulated without stimulation of overlying superficial muscles. All in all the hand control system utilizes 18 stimulation electrodes arranged in three groups of electrodes, each comprising two sets of three electrodes operating in a functionally similar manner.

FIG. 7 illustrates shoulder sensor 21, length sensor 29 and pressure sensor 30, the functions of which have been described above. Output signals from those sensors are applied, together with a signal from a potentiometer 40, to an analog to digital converter 64. Digitized output signals from analog to digital converter 64 are applied to computer 60 which produces three digital output signals representing the amplitude of the desired stimulation for the hand flexors, thumb flexors, and wrist extensors. Those three signals are applied to digital to analog converters 61 through 63 which generate analog signals for application to stimulation circuits 71 through 73 respectively. Stimulation circuits 71 through 73 are of identical construction and all receive clock signals from a stimulation clock 65. Stimulation clock 65 is responsible for the timing of the signals described above in connection with FIG. 13. The amplitudes of the pulses illustrated in that figure are controlled by the output signals from computer 60.

Figure 8A:
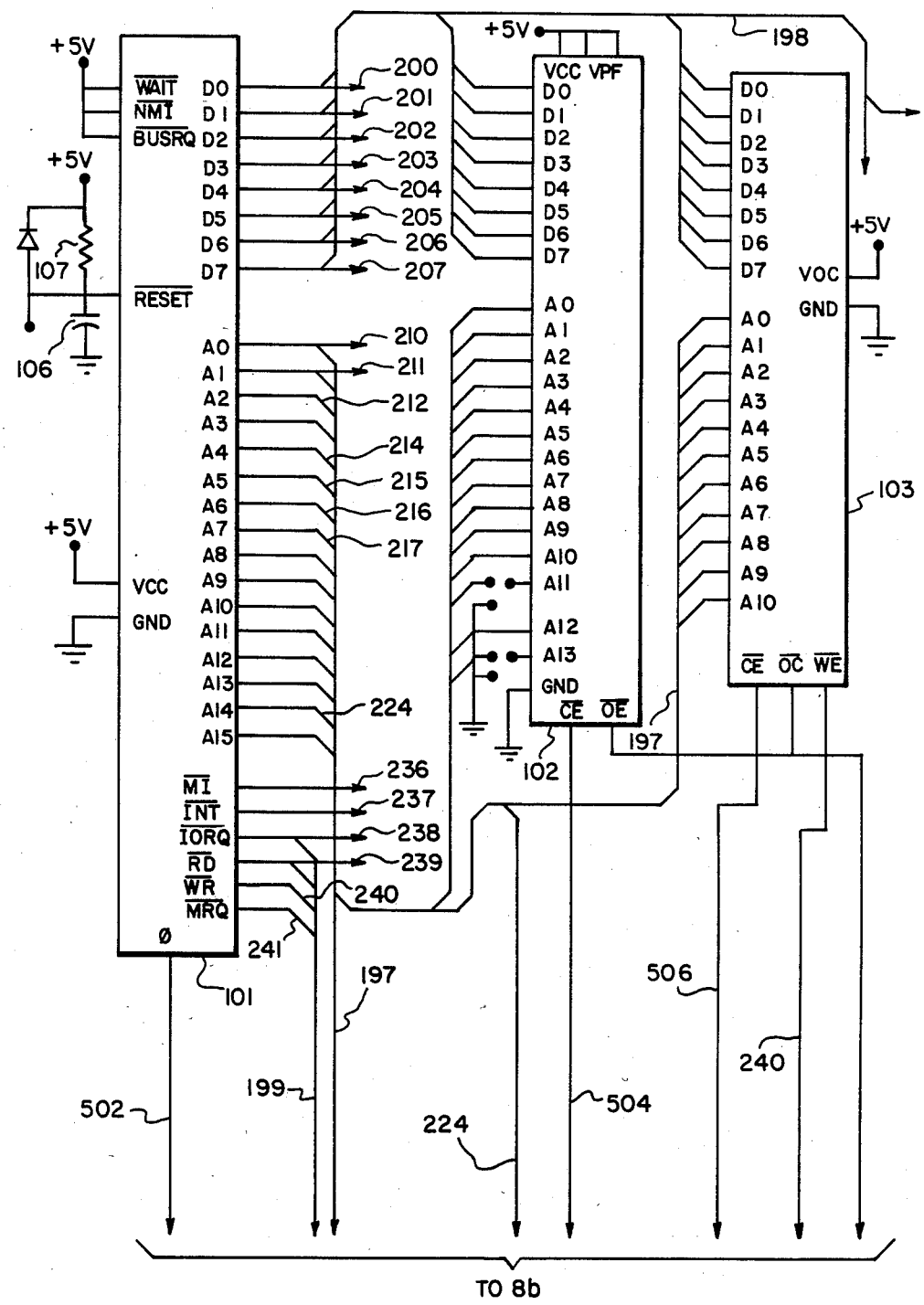
Figure 9:
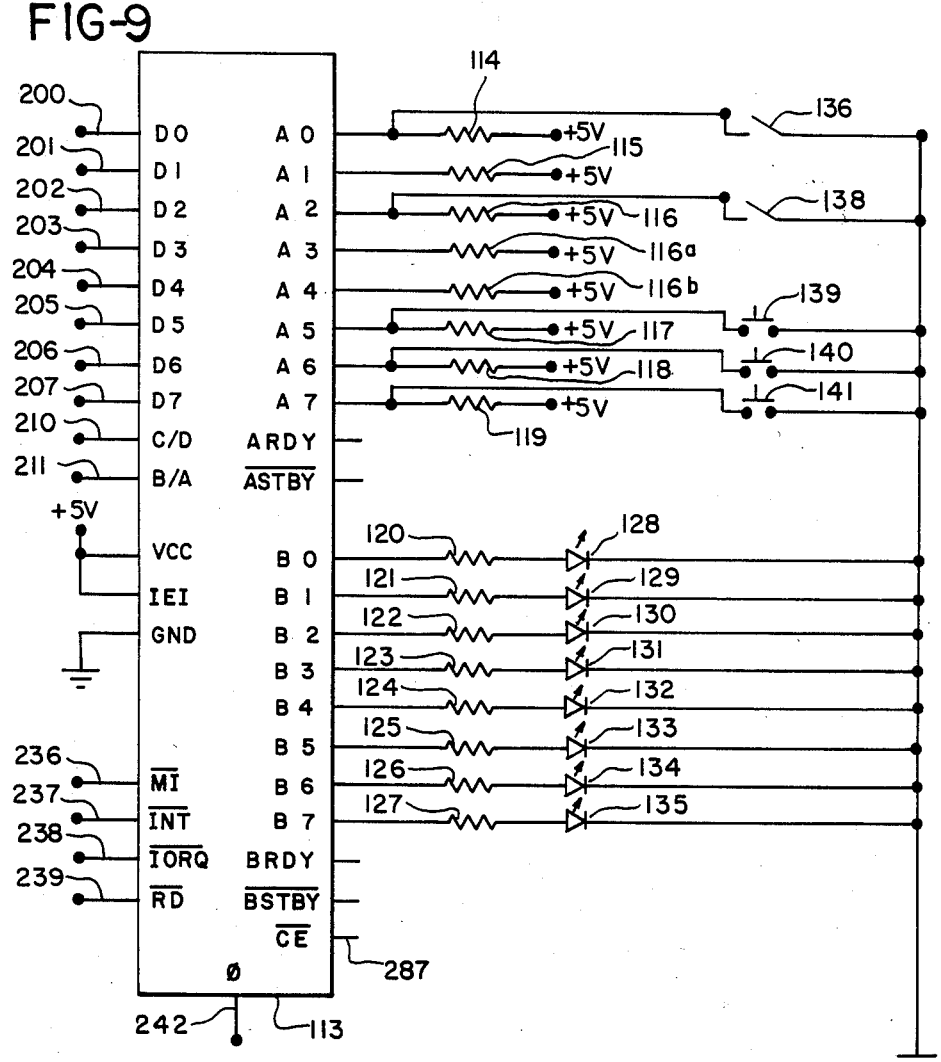
FIG. 9 is a schematic diagram of a parallel input/out port for interfacing the computer components of FIG. 8 with a control panel.

FIGS. 8a, 8b and 9 collectively illustrate the components comprising computer 60. The major components as illustrated therein are a Z80 microprocessor 101, an EPROM 102, a read/write memory 103, a decoder/demultiplexor 104, a J-K flip-flop 105, a two MHz crystal oscillator 108 and a Z80-PIO parallel port 113. Table I presents detailed data for above components as well as other components illustrated in FIGS. 8 through 12.

TABLE I

| Ref. No | Component Data Description |
|---|---|
| 25 | ECG electrode 01-3330 (NDM Corp.) |
| 26 | ECG electrode 01-3330 (NDM Corp.) |
| 27 | 10K Ω shoulder pot. |
| 29 | 10K Ω length pot. |
| 30 | 10K Ω to 15K Ω variable resistance pressure sensor |
| 31 | Stimulation Electrode MEDTRONIC 3795 |
| 40 | 10K Ω |
| 44 | 5K Ω |
| 45 | 5K Ω |
| 46 | 5K Ω |
| 61 | DAC 0832 D,A converter (National Semiconductor) |
| 62 | DAC 0832 D,A converter (National Semiconductor) |
| 63 | DAC 0832 D,A converter (National Semiconductor) |
| 64 | ADC 0808 A,D converter (National Semiconductor) |
| 101 | Z80 microprocessor (Zilog, Inc.) |
| 102 | 2716 EPROM (Zilog, Inc.) |
| 103 | 6116 Read, Write Memory (Hitachi) |
| 104 | SN74LS138 Decoder,Demultiplexer (Texas Instruments) |
| 105 | SN74LS73 flip-flop (Texas Instruments) |
| 106 | 68 μf |
| 107 | 10K Ω |
| 108 | 2 MHz oscillator |

TABLE I-continued

| Ref. No | Component Data Description |
|---|---|
| 109 | 0.1 μf |
| 110 | 0.1 μf |
| 111 | 0.1 μf |
| 112 | 0.1 μf |
| 113 | Z80-PIO parallel I,O port (Zilog, Inc.) |
| 114–119 | 10K Ω |
| 120–127 | 150 Ω |
| 305–312 | 2N3904 |
| 313–316 | 2SC1308 |
| 321–324 | 470 Ω |
| 329–332 | 470 Ω |
| 333–336 | 1K Ω |
| 337–340 | 100 Ω |
| 325–328 | 10K Ω |
| 333,336 | 1K Ω |
| 337–340 | 100Ω |
| 350–356 | SE, NE 555 (Signetics) |
| 360, 361 | 100K Ω |
| 362 | 0.1 μf |
| 363 | 0.001 μf |
| 364, 365 | 10 K Ω |
| 366 | .001 μf |
| 357 | 2N3904 |
| 367 | 22K Ω |
| 368 | 10K Ω |
| 369 | 0.1 μf |
| 370 | .001 μf |
| 370a | 10K μ |
| 371 | 10K Ω |
| 372 | 10K Ω |
| 373 | 0.1 μf |
| 374, 375 | 22K Ω |
| 376 | 10K Ω |
| 377 | 0.1 μf |
| 378–380 | 10K Ω |
| 381 | 0.1 μf |
| 382 | 10K Ω |
| 383 | 22K Ω |
| 384 | 0.001 μf |
| 385 | 0.1 μf |
| 386, 387 | 0.001 μf |
| 388 | 10K Ω |
| 389 | 0.1 μf |
| 389a | 22K Ω |
| 390–397 | 100K Ω |
| 398 | 10K Ω |
| 399 | 100K Ω |
| 400 | 100KHz oscillator |
| 401 | 0.1 μf |
| 409 | 1K Ω |

Microprocessor 101 is connected to eight data lines 200 through 207 collectively forming a data bus identified by the reference numeral 198. Microprocessor 101 also has 16 address lines which collectively form an address bus 197. Two of these address lines, lines 210 and 211 are connected to the C/D and B/A terminals of parallel port 113. A HI signal on line 210 conditions parallel port 113 for organization of its internal registers in accordance with data applied to data terminals D0 through D7. This feature is utilized to set up parallel port 113 for reception of input data at terminals A0 through A7 and transmission of output data at terminals B0 through B7. A LO signal on line 210 conditions parallel port 113 to connect data terminals D0 through D7 for communication on a selective basis with either of terminal set A0 through A7 or B0 through B7 depending upon the state of the signal on line 211. A HI signal on line 211 selects B terminal communication while a LO signal selects A terminal communication.

When the A terminals of parallel port 113 are selected, then upon reception of a chip select signal on line 287, switches 136, 138, 139, 140 and 141 are read, and a corresponding eight-bit data word is relayed to the data terminals for transmission to microprocessor 101 on data lines 200 through 207. Alternatively, selection of the B terminals causes the bits in a data word from microprocessor 101 to produce illumination of corresponding ones of light emitting diodes 128 through 135. This operation is controlled by the assembly level instructions "OUT LIGHTS" and "IN SWITCHES". The entire program for controlling operation of microprocessor 101 is stored in memory units 102 and 103. That program is listed below in Table II.

Crystal oscillator 108 provides a clock for operation of microprocessor 101 and flip-flop 105. A clock signal is also provided on line 242 for application to parallel port 113. Also as illustrated in FIGS. 8a, 8b and 9, parallel port 113 is connected to lines 236 through 239 from microprocessor 101 for purposes of normal operating control.

Decoder/demultiplexor 104 is connected via lines 214 through 217 to address terminals A4 through A7 of microprocessor 101. This provides a four-bit address code for activation of one of eight output lines 280 through 287. Line 287 is connected to the chip selection terminal of parallel port 113 to cause the above-described operation of the parallel port upon generation of hexadecimal address F2 by microprocessor 101. Addresses 90, AO and BO cause activation of decoder output lines 281, 282 and 283 for selection of D/A converters 61, 62 and 63 respectively (hand, thumb and extensor stimulation). Decoder output lines 280, 284 and 285 are not utilized.

Flip-flop 105 produces output pulses on line 276 for use as a clock by A/D converter 64. As illustrated by a small inset on FIG. 8b all power supplies are filtered through a series of 0.1 microfara capacitors to eliminate system noise.

Microprocessor 101 also selects feedback signals for transmission by A/D converter 64. This selection is made by means of a three-bit address code on lines 210 through 212 of address bus 197. The hexadecimal code E1 selects the shoulder sensor, while E2 selects the pressure sensor and E3 selects the length sensor. The code E4 selects potentiometer 40 which is appropriately adjusted during system programming for setting of the maximum permitted stimulation level. The hexadecimal code EO selects the analog input which indicates satisfactory attachment of the shoulder sensor to the skin of the wearer. An address code of FO is directly applied to parallel port 113 for chip selection, as described above.

Figure 10:
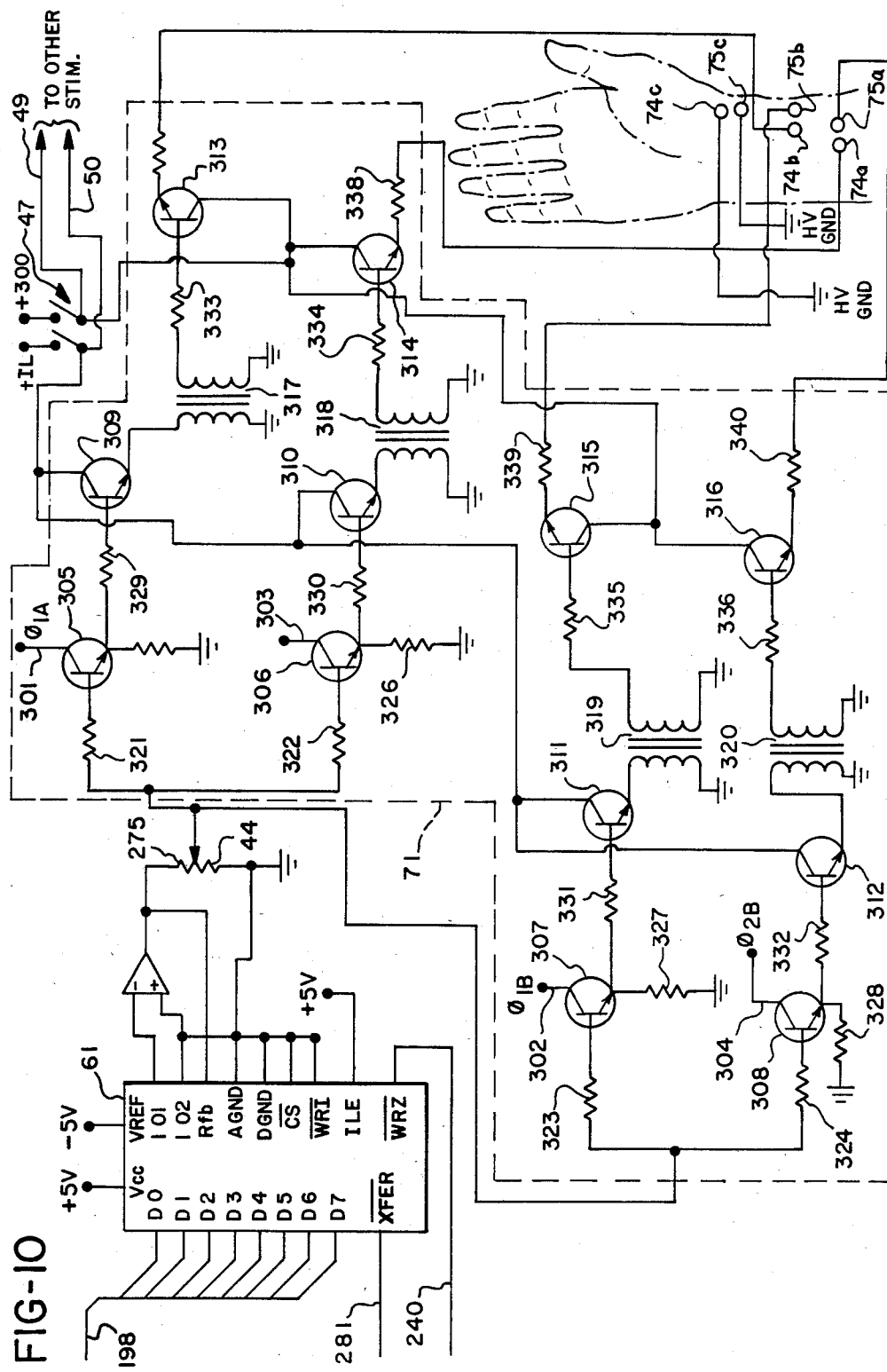
FIG. 10 is a schematic illustration of a stimulation channel including a digital to analog converter and a stimulation driver.

As noted above, computer 60 generates digital codes on data bus 198 which represent desired stimulation amplitudes for the three muscle groups to be stimulated. Those codes are applied to D/A converters 61 through 63, as selected by decoder 104. FIG. 10 illustrates the details of one stimulation channel including D/A converter 61, hand flexor stimulator 71 and stimulation electrodes 74a through 75c. The circuits for stimulating the thumb and the extensor are similar and are not illustrated in detail.

Referring now to FIG. 10, D/A converter 61 is selected for operation by a selection signal appearing on line 281 from the Y1 terminal of decoder 104 (address code 90 hex). A write control signal is also received from microprocessor 101 via line 240. Stimulation amplitude codes are applied by data bus 198 to the data terminals of D/A converter 61, and analog representations thereof appear across potentiometer 275. Potentiometer 44 and similar potentiometers (44,46) at the output sides of D/A converters 62 and 63 are individually adjusted as part of a calibration procedure performed on a daily basis for the particular quadriplegic person utilizing the equipment. Calibration is carried out by placing the hexadecimal number 40 into the accumulator of microprocessor 101 and outputting that number to all three muscle control channels. The potentiometers are adjusted during reception of that particular driving signal so as to produce a slight muscle twitch indicating application of a threshold stimulation voltage.

Output signals from potentiometer 44 are applied to the base terminals of transistors 305, 306, 307 and 308. Concomitantly timing pulses from stimulation clock 65 are applied to lines 301, 303, 302 and 304 for application to the collector terminals of transistors 305, 306, 307 and 308 respectively. As a result thereof, transistors 305 through 308 generate emitter currents across resistors 329 through 332 for application to the base terminals of transistors 309 through 312. Transistors 309 through 312 generate a series of pulses across the primary windings of transformers 317 through 320. The signals so applied across the primary windings of transformers 317 through 320 have the general form illustrated in FIG. 13. The signals so produced comprise a series of pulses having maximum amplitudes which may range between 0 and 12 volts. These signals across the primary windings of transformers 317 through 320 cause production of low current, high voltage pulses ranging from 0 to 255 volts across the secondary windings of the transformers. The second windings of the transformers have one side grounded to a high voltage ground which is different from the ground utilized for the primary windings thereof. The output pulses from the secondary windings are thereby RF isolated to maintain the safety of the quadriplegic person.

Output voltages from transformers 317 through 320 are applied to the base terminals of transistors 313 through 316 respectively. Transistors 313 through 316 provide a current gain so as to have high current, high voltage and low duty cycle pulses available for application across the pairs of electrode terminals which are serviced thereby.

Figure 11:
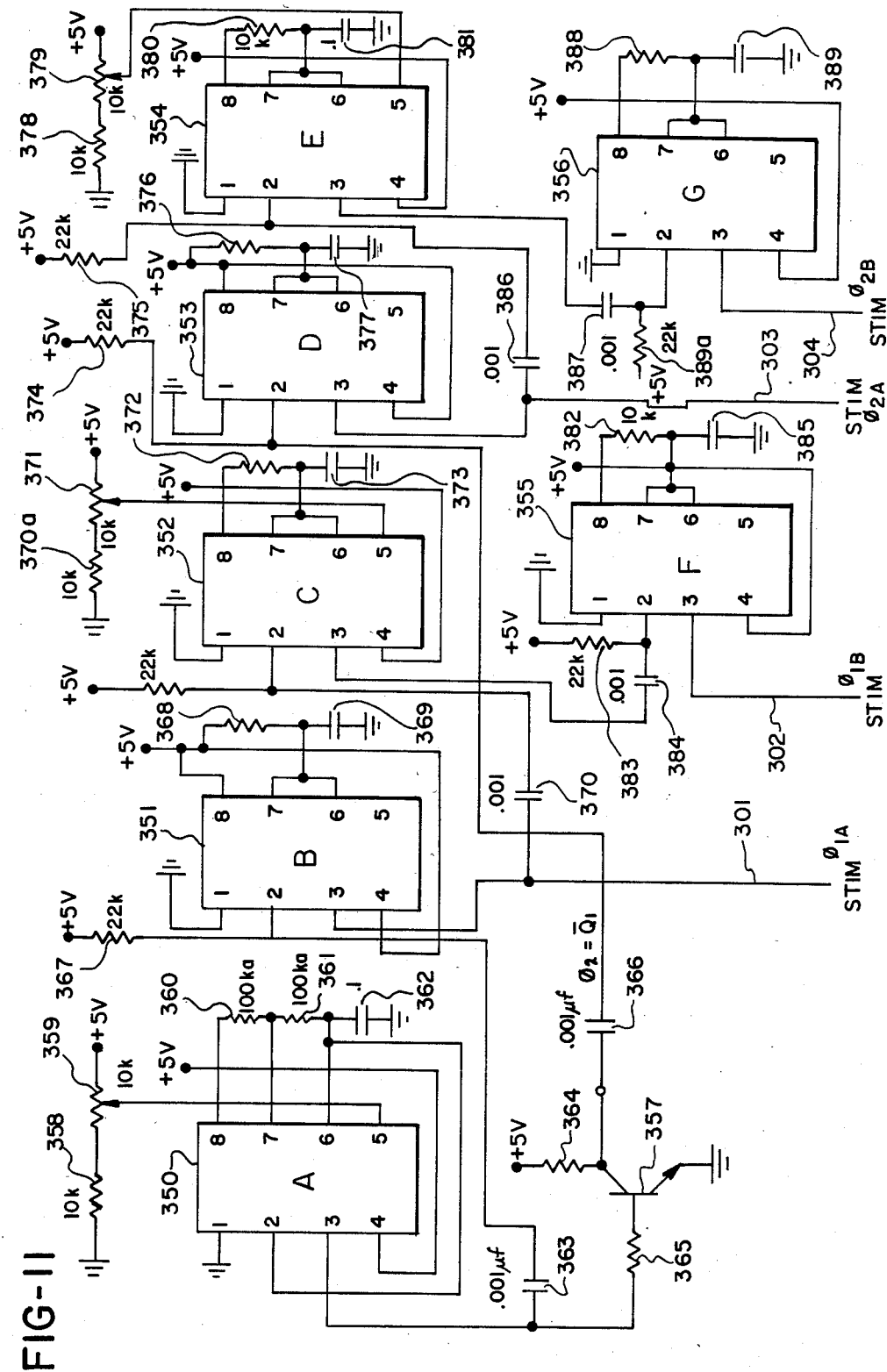
FIG. 11 is a schematic diagram of a stimulation clock.

FIG. 11 illustrates the details of stimulation clock 65. As illustrated in FIG. 11, the circuit comprises seven SE/NE555 timers 350 through 356. Timer 350 is the clock oscillator for the circuit. Pin 5 of timer 350 is attached to a potentiometer arrangement including two 10K resistors. The potentiometer is adjusted for control of the basic stimulation frequency which may run between 20 and 60 Hz, 60 Hz being preferred.

The output of timer 350 is inverted by transistor 357 to provide a clock phase I and a clock phase II signal. The phase I and phase II signals excite timers 351 and 353 respectively. These timers are set up as one shot multi-vibrators in contrast to the free running operation of timer 350. Timers 351 and 353 provide output pulses which are 180° out of phase. Resistors 368 and 376 and capacitors 369 and 377 cause those pulses to have a pulse width of 300 microseconds. These pulses are applied to lines 301 and 303 for timing control of waveforms 402 and 403 of FIG. 13.

The pulses applied to lines 301 and 303 are also applied to timers 352 and 354 respectively. These latter two timers are delay timers having terminals No. 5 thereof connected to potentiometer arrangements as illustrated in FIG. 11. Depending upon the setting of those potentiometers, timers 353 and 354 are able to produce delays ranging from about 180 microseconds to just over one millisecond. Output signals from timers 352 and 354 trigger timers 355 and 356 respectively, which are set up as one shot multi-vibrators. Timers 355 and 356 produce output signals on lines 302 and 304 which time the generation of the pulses illustrated by waveforms 404 and 405 of FIG. 13.

FIG. 12 illustrates the details of electrical connections for A/D converter 64. That converter has five input lines connected for receiving five different analog signals, as above described. Input signals on lines 210 through 212 of address bus 197 select a desired analog signal for digitizing. The digitized signal is transmitted to data bus 198 for relay to microprocessor 101.

The program listing, as set forth in Table II, is written in 8080 assembly language. The program, when assembled, will run on a Z80 microprocessor. The program includes a common stem program, a pressure sub-routine and a length sub-routine. The pressure or length sub-routines are selected by activating one or the other of switches 136 or 138 on control panel 43. These switches are checked at program lines 304 and 307, and sub-routine entries are made at those points as appropriate.

For all operating modes the program requires threshold settings of potentiometers 44–46, as described above. This sets the gain of stimulators 71–73 to produce threshold stimulation for a stimulation command of 40 (hexadecimal). This is followed by a setting of potentiometers 40 which generates analog input signals effectively simulating shoulder movement. During this part of the programming a series of settings of potentiometer 40 are made, read and digitized. A hexadecimal value of 40 (threshold set) is added to each digitized result, and the sum is output for generation of a stimulation signal. Settings of potentiometer 40 are gradually increased until the subject feels that the stimulation level is uncomfortable. The computer stores the digitized value of the analog input which produces such a condition and thereafter treats that value as a maximum shoulder command signal. Shoulder commands which exceed the maximum value, so determined, are ignored.

This is a safety procedure to prevent pain or injury to the subject.

After the setting of the potentiometers has taken completed the program enters the routine beginning at line 268, wherein the subject calibrates the zero position of the shoulder sensor. During this routine the quadriplegic person moves his shoulder back and forth until a comfortable middle position has been achieved. At this point push button 141 is depressed to signal the computer that this position is to be used as a zero point. When the shoulder moves back from this position the hand opens. If it is moved in the forward direction the hand will close. The greater the forward movement, the greater the hand closure. This provides full open-loop control of the hand with feedback being provided by the human eye and the nerves in the fingers.

Following zeroing of the shoulder sensor the program checks to ascertain the position of switches 136 and 138 in order to determine whether or not the open loop hand control routine should be supplanted by closed loop control using feedback signals from length sensor 23 or pressure sensor 30. The sub-routines for pressure and length feedback commence at line numbers 409 and 461 respectively. In these closed loop routines the signal from the shoulder sensor is subtracted from the feedback signal to develop an error signal (program lines 419 and 472). If the error signal is negative, then the stimulation voltage is increased. Thus the shoulder is used to generate pressure or length commands.

As described above the computer periodically checks for attachment of shoulder sensor 21 to the skin of the subject. This check is made at line 331. If that check indicates that the sensor is loose, then the program jumps into an error routine beginning at line 357.

While the method herein described, and the form of apparatus for carrying this method into effect, constitute preferred embodiments of this invention, it is to be understood that the invention is not limited to this precise method and form of apparatus, and that changes may be made in either without departing from the scope of the invention, which is defined in the appended claims.

TABLE II

```
 1:
 2:
 3:
 4:
 5:
 6:
 7:
 8:
 9:            ;*** PARALLEL OUTPUT PORT BIT
               DESIGNATIONS ***
10:
11:            ;ALL BITS ARE ACTIVE HIGH
12:
13:            ;BIT 0=SYSTEM INACTIVE
14:            ;BIT 1-THRESHOLD SET
15:            ;BIT 2=MAX VOLTAGE SET
16:            ;BIT 3-ZERO SENSOR SET
17:            ;BIT 4=SYSTEM ON
18:            ;BIT 5=MEASURING
19:            ;BIT 6=RIGHT SWITCH
20:            ;BIT 7=LEFT SWITCH
21:
22:
23:            ;*** PARALLEL INPUT PORT BIT
               DESIGNATIONS***
24:
25:            ;ALL SWITCHES ACTIVE LOW
26:
27:
```

TABLE II-continued

```
28:                 ;BIT 0 = FEEDBACK CONTROL PRESSURE
29:                 ;BIT 2 = FEEDBACK CONTROL LENGTH
30:                 ;BIT 5 = RESET FOR COMPUTER
31:                 ;BIT 6 = LEFT BUTTON
32:                 ;BIT 7 = RIGHT BUTTON
33:
34:                 ;*** INPUT PORT NUMBERS ***
35:
36:                 ;0E0H = SENSOR CHECK
37:                 ;0E1H = SHOULDER SENSOR
38:                 ;0E2H = PRESSURE SENSOR
39:                 ;0E3H = LENGTH SENSOR
40:                 ;0E4H = ANALOG INPUT
41:                 ;0F0H = 8-BIT PARALLEL INPUT PORT
42:
43:                 ;*** OUTPUT PORT NUMBERS ***
44:
45:                 ;090H = HAND CONTROL
46:                 ;0A0H = THUMB CONTROL
47:                 ;0B0H = EXTENSOR CONTROL
48:                 ;0F2H = 8-BIT PARALLEL OUTPUT PORT
                    (LED'S)
49:
50:
51:                 ; REGISTER ALLOCATION
52:
53:                 ; L=HAND FLEX MAX
54:                 ; H=THUMB FLEX MAX
55:                 ; E=EXTENSOR MAX
56:                 ; C=SENSOR ZERO
57:                 ; B=TEMP STORE
58:                 ; D=PRESSURE OR HAND LENGTH
                    VOLTAGE STORE
59:
60:
61:
62:
63: 0100           START:  ORG   100H
64:
65:                 ;*****************************
66:                 ;*
67:                 ;*       INITIALIZE PORTS
68:                 ;*
69:                 ;*****************************
70:
71: 0080 =         DAC0       EQU   080H
72: 0090 =         DAC1       EQU   090H
73: 00A0 =         DAC2       EQU   0A0H
74: 00B0 =         DAC3       EQU   0B0H
75: 00C0 =         DAC4       EQU   0C0H
76: 00D0 =         DAC5       EQU   0D0H
77:
78: 00E0 =         ADC0       EQU   0E0H
79: 00E1 =         ADC1       EQU   0E1H
80: 00E2 =         ADC2       EQU   0E2H
81: 00E3 =         ADC3       EQU   0E3H
82: 00E4 =         ADC4       EQU   0E4H
83: 00E5 =         ADC5       EQU   0E5H
84: 00E6 =         ADC6       EQU   0E6H
85: 00E7 =         ADC7       EQU   0E7H
86:
87: 00F0 =         PIO$DATA$A     EQU  0F0H
88: 00F1 =         PIO$CTRL$A     EQU  0F1H
89: 00F2 =         PIO$DATA$B     EQU  0F2H
90: 00F3 =         PIO$CTRL$B     EQU  0F3H
91:
92: 4000 =         RAM            EQU      400H
93: 47FF =         RAM$TOP        EQU      RAM + 07FFH   ;**TOP
                   OF RAM**
94:
95: 00F2 =         LIGHTS     EQU    PIO$DATA$B
96: 00F0 =         SWITCHES   EQU    PIO$DATA$A
97: 00E0 =         SENSOR     EQU    ADC0
98: 00E4 =         ANALOG     EQU    ADC4
99: 0090 =         HAND       EQU    DAC1
100: 00A0 =        THUMB      EQU    DAC2
101: 00B0 =        EXTENSOR   EQU    DAC3
102: 00E1 =        SHOULDER   EQU    ADC1
103: 00E2 =        PRESS      EQU    ADC2
104: 00E3 =        LEN        EQU    ADC3
105:
106: 0100   F3                DI
```

TABLE II-continued

| | | | | | |
|---|---|---|---|---|---|
| 107: | 0101 | 31FF47 | LXI | SP,RAM$TOP | |
| 108: | | | | | |
| 109: | 0104 | AF | XRA | A | ;A = 0 |
| 110: | 0105 | D380 | OUT | DAC0 | |
| 111: | 0107 | D390 | OUT | DAC1 | |
| 112: | 0109 | D3A0 | OUT | DAC2 | |
| 113: | 010B | D3B0 | OUT | DAC3 | |
| 114: | 010D | D3C0 | OUT | DAC4 | |
| 115: | 010F | D3D0 | OUT | DAC5 | |
| 116: | | | | | |
| 117: | 0111 | 3E4F | MVI | A,4FH | ;SET PIO PORT A |
| 118: | 0113 | D3F1 | OUT | PIO$CTRL$A | ;TO INPUT |
| 119: | | | | | |
| 120: | 0115 | 3E0F | MVI | A,0FH | ;SET PIO PORT B |
| 121: | 0117 | D3F3 | OUT | PIO$CTRL$B | ;TO OUTPUT |
| 122: | | | | | |
| 123: | 0119 | FB | EI | | |
| 124: | | | | | |
| 125: | | | ;***************************************** | | |
| 126: | | | | | |
| 127: | | | | | |
| 128: | 011A | 3E00 | BARF MVI | A,00 | |
| 129: | 011C | 57 | MOV | D,A | |
| 130: | 011D | D390 | OUT | HAND | |
| 131: | 011F | D3A0 | OUT | THUMB | |
| 132: | 0121 | D3B0 | OUT | EXTENSOR | |
| 133: | 0123 | 3E41 | MVI | A,41H | |
| 134: | 0125 | D3F2 | OUT | LIGHTS | |
| 135: | 0127 | DBF0 | LOOP1 IN | SWITCHES | |
| 136: | 0129 | E620 | ANI | 20H | |
| 137: | 012B | CA1A01 | JZ | BARF | |
| 138: | 012E | DBF0 | IN | SWITCHES | |
| 139: | 0130 | E680 | ANI | 80H | |
| 140: | 0132 | C22701 | JNZ | LOOP1;LOOP IN RIGHT BUTTON NOT HIT | |
| 141: | 0135 | 3E82 | MVI | A,82H | |
| 142: | 0137 | D3F2 | OUT | LIGHTS;SET DISPLAY FOR THRESHOLD SET | |
| 143: | | | | | |
| 144: | | | | | |
| 145: | | | ; ***THRESHOLD SET*** | | |
| 146: | | | | | |
| 147: | 0139 | DBF0 | LOOP20 IN | SWITCHES | |
| 148: | 013B | E620 | ANI | 20H | |
| 149: | 013D | CA1A01 | JZ | BARF | |
| 150: | 0140 | DBF0 | IN | SWITCHES | |
| 151: | 0142 | E640 | ANI | 40H | |
| 152: | 0144 | C23901 | JNZ | LOOP20 | |
| 153: | 0147 | 3E62 | MVI | A,62H | |
| 154: | 0149 | D3F2 | OUT | LIGHTS | |
| 155: | 014B | 3E40 | MVI | A,40H;SET OUTPUT VOLTAGE | |
| 156: | 014D | D390 | OUT | HAND | |
| 157: | 014F | D3A0 | OUT | THUMB | |
| 158: | 0151 | D3B0 | OUT | EXTENSOR | |
| 159: | | | ;**THRESHOLD OFF** | | |
| 160: | | | | | |
| 161: | 0153 | DBF0 | LOOP2 IN | SWITCHES | |
| 162: | 0155 | E620 | ANI | 20H | |
| 163: | 0157 | CA1A01 | JZ | BARF | |
| 164: | 015A | DBF0 | IN | SWITCHES | |
| 165: | 015C | E680 | ANI | 80H;LEFT BUTTON HELD DOWN FOR THRESHOLD | |
| 166: | 015E | C25301 | JNZ | LOOP2 | |
| 167: | 0161 | 3E00 | MVI | A,00 | |
| 168: | 0163 | D390 | OUT | HAND | |
| 169: | 0165 | D3A0 | OUT | THUMB | |
| 170: | 0167 | 3E84 | MVI | A,84H | |
| 171: | 0169 | D3F2 | OUT | LIGHTS | |
| 172: | | | | | |
| 173: | | | ;****MAX VOLTAGE SET HAND | | |
| 174: | | | | | |
| 175: | 016B | DBF0 | LOOP3 IN | SWITCHES | |
| 176: | 016D | E620 | ANI | 20H | |
| 177: | 016F | CA1A01 | JZ | BARF | |
| 178: | 0172 | DBF0 | IN | SWITCHES | |

TABLE II-continued

| | | | | |
|---|---|---|---|---|
| 179: | 0174 | E640 | ANI | 40H |
| 180: | 0176 | C26B01 | JNZ | LOOP3;LOOK FOR MAX VOLTAGE SET HAND |
| 181: | 0179 | 3E64 | MVI | A,64H |
| 182: | 017B | D3F2 | OUT | LIGHTS;SET DISPLAY FOR HAND MAX |
| 183: | 017D | D3E4CDDE03LOOP4 | OUT | ANALOG ! CALL DELAY100 ! IN ANALOG |
| 184: | 0184 | C640 | ADI | 40H |
| 185: | 0186 | D390 | OUT | HAND |
| 186: | 0188 | DBF0 | IN | SWITCHES |
| 187: | 018A | E620 | ANI | 20H |
| 188: | 018C | CA1A01 | JZ | BARF |
| 189: | 018F | DBF0 | IN | SWITCHES |
| 190: | 0191 | E680 | ANI | 80H |
| 191: | 0193 | C27D01 | JNZ | LOOP4 |
| 192: | | | | |
| 193: | | ;**** STORE MAX HAND **** | | |
| 194: | | | | |
| 195: | 0196 | D3E4CDDE03 | OUT | ANALOG ! CALL DELAY100 ! IN ANALOG |
| 196: | 019D | 6F | MOV | L,A;STORE MAX HAND IK L |
| 197: | 019E | 3E00 | MVI | A,00 |
| 198: | 01A0 | D390 | OUT | HAND |
| 199: | 01A2 | 3E84 | MVI | A,84H |
| 200: | 01A4 | D3F2 | OUT | LIGHTS |
| 201: | | | | |
| 202: | | | | |
| 203: | | ;**** MAX VOLTAGE SET THUMB **** | | |
| 204: | | | | |
| 205: | | | | |
| 206: | 01A6 | DBF0 LOOP5 | IN | SWITCHES |
| 207: | 01A8 | E620 | ANI | 20H |
| 208: | 01AA | CA1A01 | JZ | BARF |
| 209: | 01AD | DBF0 | IN | SWITCHES |
| 210: | 01AF | E640 | ANI | 40H |
| 211: | 01B1 | C2A601 | JNZ | LOOP5 |
| 212: | 01B4 | 3E64 | MVI | A,64H |
| 213: | 01B6 | D3F2 | OUT | LIGHTS |
| 214: | 01B8 | D3E4CDDE03LOOP6 | OUT | ANALOG ! CALL DELAY100 ! IN ANALOG |
| 215: | 01BF | C640 | ADI | 40H |
| 216: | 01C1 | D3A0 | OUT | THUMB |
| 217: | | | | |
| 218: | | | | |
| 219: | 01C3 | DBF0 | IN | SWITCHES |
| 220: | 01C5 | E620 | ANI | 20H |
| 221: | 01C7 | CA1A01 | JZ | BARF |
| 222: | 01CA | DBF0 | IN | SWITCHES |
| 223: | 01CC | E680 | ANI | 80H |
| 224: | 01CE | C2B801 | JNZ | LOOP6 |
| 225: | 01D1 | D3E4CDDE03 | OUT | ANALOG ! CALL DELAY100 ! IN ANALOG |
| 226: | 01D8 | 67 | MOV | H,A |
| 227: | | ;THUMB MAX | | IN H |
| 228: | 01D9 | 3E00 | MVI | A,00 |
| 229: | 01DB | D3A0 | OUT | THUMB |
| 230: | | | | |
| 231: | | | | |
| 232: | | ;EXTENSOR | | MAX |
| 233: | | | | |
| 234: | | | | |
| 235: | 01DD | 3E84 | MVI | A,84H |
| 236: | 01DF | D3F2 | OUT | LIGHTS |
| 237: | 01E1 | DBF0 LOOP310 | IN | SWITCHES |
| 238: | 01E3 | E62C | ANI | 20H |
| 239: | 01E5 | CA1A01 | JZ | BARF |
| 240: | 01E8 | DBF0 | IN | SWITCHES |
| 241: | 01EA | E640 | ANI | 40H |
| 242: | 01EC | C2E101 | JNZ | LOOP310 |
| 243: | 01EF | 3E64 | MVI | A,64H |
| 244: | 01F1 | D3F2 | OUT | LIGHTS |
| 245: | 01F3 | D3E4CDDE03LOOP400 | OUT | ANALOG ! CALL DELAY100 ! IN ANALOG |
| 246: | 01FA | C640 | ADI | 40H |

TABLE II-continued

| | | | | |
|---|---|---|---|---|
| 247: 01FC | D3B0 | | OUT | EXTENSOR |
| 248: 01FE | DBF0 | | IN | SWITCHES |
| 249: 0200 | E620 | | ANI | 20H |
| 250: 0202 | CA1A01 | | JZ | BARF |
| 251: 0205 | D3E4CDDE03 | | OUT | ANALOG ! CALL DELAY100 ! IN ANALOG |
| 252: 020C | 5F | | MOV | E,A |
| 253: 020D | DBF0 | | IN | SWITCHES |
| 254: 020F | E680 | | ANI | 80H |
| 255: 0211 | C2F301 | | JNZ | LOOP400 |
| 256: 0214 | 3E88 | | MVI | A,88H |
| 257: 0216 | D3F2 | | OUT | LIGHTS |
| 258: 0218 | DBF0 | LOOP7 | IN | SWITCHES |
| 259: 021A | E620 | | ANI | 20H |
| 260: 021C | CA1A01 | | JZ | BARF |
| 261: 021F | DBF0 | | IN | SWITCHES |
| 262: 0221 | E640 | | ANI | 40H |
| 263: 0223 | C21802 | | JNZ | LOOP7 |
| 264: 0226 | 3E68 | | MVI | A,68H |
| 265: 0228 | D3F2 | | OUT | LIGHTS;SET OUTPUT ACTIVE |
| 266: | | | | |
| 267: | | | | |
| 268: | | ;**SET SENSOR ZERO** | | |
| 269: | | | | |
| 270: | | | | |
| 271: 022A | DBF0 | LOOP8 | IN | SWITCHES |
| 272: 022C | E620 | | ANI | 20H |
| 273: 022E | CA1A01 | | JZ | BARF |
| 274: 0231 | DBF0 | | IN | SWITCHES |
| 275: 0233 | E680 | | ANI | 80H |
| 276: 0235 | C22A02 | | JNZ | LOOP8 |
| 277: 0238 | D3E1CDDE03 | | OUT | SHOULDER ! CALL DELAY100 ! IN SHOULDER |
| 278: 023F | C600 | | ADI | 00 |
| 279: 0241 | FAC602 | | JM | LOOP300 |
| 280: 0244 | 4F | LOOP301 | MOV | C,A |
| 281: | | ;C | REGISTER | =SENSOR 0 |
| 282: | | | | |
| 283: | | | | |
| 284: | | ;**START HAND CONTROL** | | |
| 285: | | | | |
| 286: | | | | |
| 287: 0245 | 3E90 | | MVI | A,90H |
| 288: 0247 | D3F2 | | OUT | LIGHTS |
| 289: 0249 | DBF0 | LOOP9 | IN | SWITCHES |
| 290: 024B | E640 | | ANI | 40H |
| 291: 024D | C24902 | | JNZ | LOOP9;CHECK FOR START WORK |
| 292: 0250 | 3E70 | | MVI | A,70H |
| 293: 0252 | D3F2 | | OUT | LIGHTS,SET SYSTEM ACTIVE |
| 294: 0254 | 3E00 | | MVI | A,0 |
| 295: 0256 | 57 | | MOV | D,A |
| 296: 0257 | DBF0 | LOOP10 | IN | SWITCHES ;CHECK FOR RESET |
| 297: 0259 | E620 | | ANI | 20H |
| 298: 025B | CA1A01 | | JZ | BARF |
| 299: 025E | D3E1CDDE03 | | OUT | SHOULDER ! CALL DELAY100 ! IN SHOULDER |
| 300: 0265 | 91 | | SUB | C |
| 301: 0266 | FAAA02 | | JM | LOOP201; LOOP OUT IF SENSOR NOT AT THRESHOLD |
| 302: 0269 | 47 | | MOV | B,A |
| 303: | | ;CHECK FOR NO FEEDBACK OR FEEDBACK | | |
| 304: 026A | DBF0 | | IN | SWITCHES |
| 305: 026C | E600 | | ANI | 1 |
| 306: 026E | CA1903 | | JZ | PRESSURE |
| 307: 0271 | DBF0 | | IN | SWITCHES |
| 308: 0273 | E604 | | ANI | 4 |
| 309: 0275 | CA7C03 | | JZ | LENGTH ; RETURN TO LOOP10 AFTER SUBROUTINE |
| 310: | | ;TEMP | STORE | OF OUT VOLTAGE |
| 311: 0278 | 78 | | MOV | A,B |
| 312: 0279 | 94 | | SUB | H;CHECK THUMB MAX |
| 313: 027A | F28602 | | JP | LOOP11 |

TABLE II-continued

| | | | | |
|---|---|---|---|---|
| 314: 027D | 78 | | MOV | A,B |
| 315: 027E | C640 | | ADI | 40H |
| 316: 0280 | D3A0 | | OUT | THUMB |
| 317: 0282 | 3E00 | | MVI | A,00 |
| 318: 0284 | D3B0 | | OUT | EXTENSOR |
| 319: 0286 | 78 | LOOP11 | MOV | A,B |
| 310: 0287 | 95 | | SUB | L;CHECK HAND MAX |
| 321: 0288 | F29402 | | JP | LOOP12 |
| 322: 0288 | 78 | | MOV | A,B |
| 323: 028C | C640 | | ADI | 40H |
| 324: 028E | D390 | | OUT | HAND |
| 325: 0290 | 3E00 | | MVI | A,00 |
| 326: 0292 | D3B0 | | OUT | EXTENSOR |
| 327: | | | | |
| 328: | | | | |
| 329: | | ;**CHECK END HAND** | | |
| 330: | | | | |
| 331: 0294 | D3E0CDDE03 | LOOP12 | OUT | SENSOR ! CALL DELAY100 ! IN SENSOR; CHECK FOR LOOSE SENSOR |
| 332: 029B | FE1E | | CPI | 30 |
| 333: 029D | F2CB02 | | JP | ERROR; SENSOR LOOSE |
| 334: 02A0 | DBF0 | | IN | SWITCHES |
| 335: 02A2 | E680 | | ANI | 80H |
| 336: 02A4 | C25702 | | JNZ | LOOP10 |
| 337: 02A7 | C31A01 | | JMP | BARF |
| 338: | | ;SET EXTENSOR AND ZERO FLEXORS | | |
| 339: 02AA | 3E00 | LOOP201 | MVI | A,00 |
| 340: 02AC | D390 | | OUT | HAND |
| 341: 02AE | D3A0 | | OUT | THUMB |
| 342: 02B0 | 57 | | MOV | D,A |
| 343: 02B1 | D3E1CDDE03 | | OUT | SHOULDER ! CALL DELAY100 ! IN SHOULDER |
| 344: 02B8 | 91 | | SUB | C |
| 345: 02B9 | C60A | | ADI | 10 |
| 346: 02BB | F25702 | | JP | LOOP10 |
| 347: 02BE | 7B | | MOV | A,E |
| 348: 02BF | D614 | | SUI | 2 |
| 349: 02C1 | D3B0 | | OUT | EXTENSOR |
| 350: 02C3 | C35702 | | JMP | LOOP10 |
| 351: | | | | |
| 352: 02C6 | 3E00 | LOOP300 | MVI | A,00 |
| 353: 02C8 | C34402 | | JMP | LOOP301 |
| 354: | | | | |
| 355: | | | | |
| 356: | | | | |
| 357: | | ;**ERROR ELECTRODE LOOSE** | | |
| 358: | | | | |
| 359: | | | | |
| 360: 02CB | 3E00 | ERROR | MVI | A,00 |
| 361: 02CD | D370 | | OUT | 112 |
| 362: 02CF | D390 | | OUT | HAND |
| 363: 02D1 | D3A0 | | OUT | THUMB |
| 364: 02D3 | D3B0 | | OUT | EXTENSOR |
| 365: 02D5 | 5F | | MOV | E,A |
| 366: 02D6 | 3EFF | | MVI | A,255 |
| 367: 02D8 | D3F2 | | OUT | LIGHTS |
| 368: 02DA | DBF0 | | IN | SWITCHES |
| 369: 02DC | E620 | | ANI | 20H |
| 370: 02DE | CA1A01 | | JZ | BARF |
| 371: 02E1 | 3E00 | | MVI | A,00 |
| 372: | | | | |
| 373: | | ;FLASH | | |
| 374: | | | | |
| 375: 02E3 | C601 | ERROR1 | ADI | 01 |
| 376: 02E5 | C2E302 | | JNZ | ERROR1 |
| 377: 02E8 | 7B | | MOV | A,E |
| 378: 02E9 | C601 | | ADI | 01 |
| 379: 02EB | 5F | | MOV | E,A |
| 380: 02EC | C2E302 | | JNZ | ERROR1 |
| 381: 02EF | 3E00 | ERROR2 | MVI | A,00 |
| 382: 02F1 | 5F | | MOV | E,A |
| 383: 02F2 | 3E00 | | MVI | A,00 |
| 384: 02F4 | D3F2 | | OUT | LIGHTS |
| 385: 02F6 | DBF0 | | IN | SWITCHES |
| 386: 02F8 | E620 | | ANI | 20H |
| 387: 02FA | CA1A01 | | JZ | BARF |
| 388: 02FD | 3E00 | | MVI | A,00 |
| 389: 02FF | C601 | ERROR3 | ADI | 01 |
| 390: 0301 | 00 | | NOP | |

TABLE II-continued

| | | | | |
|---|---|---|---|---|
| 391: | 0302 | 00 | | NOP |
| 392: | 0303 | 00 | | NOP |
| 393: | 0304 | 00 | | NOP |
| 394: | 0305 | 00 | | NOP |
| 395: | 0306 | 00 | | NOP |
| 396: | 0307 | 00 | | NOP |
| 397: | 0308 | 00 | | NOP |
| 398: | 0309 | 00 | | NOP |
| 399: | 030A | 00 | | NOP |
| 400: | 030B | 00 | | NOP |
| 401: | 030C | C2FF02 | | JNZ ERROR3 |
| 402: | 030F | 7B | | MOV A,E |
| 403: | 0310 | C601 | | ADI 01 |
| 404: | 0312 | 5F | | MOV E,A |
| 405: | 0313 | C2FF02 | | JNZ ERROR3 |
| 406: | 0316 | C3CB02 | | JMP ERROR |
| 407: | | | | |
| 408: | | | | |
| 409: | | ; | | PRESSURE SUBROUTINE |
| 410: | | | | |
| 411: | 0319 | 00 | PRESSURE | NOP; INCREMENT OUTPUT PRESSURE NUMBER |
| 412: | 031A | D3E1CDDE03 | | OUT SHOULDER ! CALL DELAY100 ! IN SHOULDER |
| 413: | 0321 | C600 | | ADI 0 |
| 414: | 0323 | FA5702 | | JM LOOP10 |
| 415: | 0326 | D614 | | SUI 20; THRESHOLD FOR SHOULDER SENSOR |
| 416: | 0328 | FA5702 | | JM LOOP10 ; JUMP IF SENSOR NOT PAST THRESHOLD |
| 417: | 032B | 47 | | MOV B,A |
| 418: | 032C | D3E2CDDE03 | | OUT PRESS ! CALL DELAY100 ! IN PRESS; INPUT SENSOR FOR PRESSURE |
| 419: | 0333 | 90 | | SUB B |
| 420: | 0334 | FA4E03 | | JM ROUND10; INCREASE |
| 421: | 0337 | 7A | | MOV A,D |
| 422: | 0338 | D601 | | SUI 1 |
| 423: | 033A | FA9402 | | JM LOOP12 |
| 424: | 033D | 57 | | MOV D,A |
| 425: | 033E | C640 | | ADI 40H |
| 426: | 0340 | D390 | | OUT HAND |
| 427: | 0342 | D3A0 | | OUT THUMB |
| 428: | 0344 | 3E00 | | MVI A,0 |
| 429: | 0346 | C601 | ROUND20 | ADI 1 |
| 430: | 0348 | C24603 | | JNZ ROUND20 ; DELAY |
| 431: | 034B | C39402 | | JMP LOOP12 |
| 432: | 034B | 00 | ROUND10 | NOP ; GO ON |
| 433: | 034F | 7A | | MOV A,D |
| 434: | 0350 | C601 | | ADI 1 |
| 435: | 0352 | FA5702 | | JM LOOP10 ; OVERFLOW SO GET OUT |
| 436: | 0355 | 57 | | MOV D,A |
| 437: | 0356 | 78 | | MOV A,B |
| 438: | 0357 | 94 | | SUB H ; CHECK THUMB MAX |
| 439: | 0358 | F26403 | | JP LOOP114 |
| 440: | 035B | 78 | | MOV A,B |
| 441: | 035C | C640 | | ADI 40H |
| 442: | 035E | D3A0 | | OUT THUMB |
| 443: | 0360 | 3E00 | | MVI A,0 |
| 444: | 0362 | D3B0 | | OUT EXTENSOR |
| 445: | 0364 | 78 | LOOP114 | MOV A,B |
| 446: | 0365 | 95 | | SUB L ;CHECK HAND MAX |
| 447: | 0366 | F27203 | | JP LOOP123 |
| 448: | 0369 | 78 | | MOV A,B |
| 449: | 036A | C640 | | ADI 40H |
| 450: | 036C | D390 | | OUT HAND |
| 451: | 036E | 3E00 | | MVI A,0 |
| 452: | 0370 | D3B0 | | OUT EXTENSOR |
| 453: | 0372 | 3E00 | LOOP123 | MVI A,0 ; DELAY |
| 454: | 0374 | C601 | LOOP124 | ADI 1 |
| 455: | 0376 | C27403 | | JNZ LOOP124 |
| 456: | 0379 | C39402 | | JMP LOOP12 |
| 457: | | | | |
| 458: | | | | |
| 459: | | | | |
| 460: | | | | |
| 461: | | ; | | LENGTH SUBROUTINE |

TABLE II-continued

| | | | | | |
|---|---|---|---|---|---|
| 462: | | | | | |
| 463: | | | | | |
| 464: | 037C | 00 | LENGTH | NOP | ; INCREMENT OUTPUT BY LENGTH |
| 465: | 037D | D3E1CDDE03 | | OUT | SHOULDER ! CALL DELAY100 IN SHOULDER; INPUT LENGTH OF FINGERS - FLEX NUMBER |
| 466: | 0384 | C600 | | ADI | 0 |
| 467: | 0386 | FA5702 | | SUI | LOOP10 |
| 468: | 0389 | D614 | | SUI | 20 ; THRESHOLD FOR LENGTH SENSOR |
| 469: | 038B | FA5702 | | JM | LOOP10; JUMP OUT IF SENSOR NOT 0 |
| 470: | 038E | 47 | | MOV | E,A |
| 471: | 038F | D3E3CDDE03 | | OUT | LEN ! CALL DELAY100 ! IN LEN ; OUTPUT LENGTH OF FINGER |
| 472: | 0396 | 90 | | SUB | B |
| 473: | 0397 | FAB103 | | JM | ROUND1 ; INCREASE VOLTS |
| 474: | 039A | 7A | | MOV | A,D |
| 475: | 039B | D601 | | SUI | 1 |
| 476: | 039D | FA9402 | | JM | LOOP12 |
| 477: | 03A0 | 57 | | MOV | D,A |
| 478: | 03A1 | C640 | | ADI | 40H |
| 479: | 03A3 | D390 | | OUT | HAND |
| 480: | 03A5 | D3A0 | | OUT | THUMB |
| 481: | 03A7 | 3E00 | | MVI | A,0 |
| 482: | 03A9 | C601 | ROUND2 | ADI | 1 |
| 483: | 03AB | C2A903 | | JNZ | ROUND2 ; DELAY |
| 484: | 03AE | C39402 | | JMP | LOOP12 |
| 485: | 03B1 | 00 | ROUND1 | NOP | ; GO ON |
| 486: | 03B2 | 7A | | MOV | A,D |
| 487: | 03B3 | C601 | | ADI | 1 |
| 488: | 03B5 | FA5702 | | JM | LOOP10 ; OVERFLOW, SO GET OUT |
| 489: | 03B8 | 78 | | MOV | A,B |
| 490: | 03B9 | 94 | | SUB | H ; CHECK THUMB MAX |
| 491: | 03BA | F2C603 | | JP | LOOP214 |
| 492: | 03BD | 78 | | MOV | A,B |
| 493: | 03BE | C640 | | ADI | 40H |
| 494: | 03C0 | D3A0 | | OUT | THUMB |
| 495: | 03C2 | 3E00 | | MVI | A,0 |
| 496: | 03C4 | D3B0 | | OUT | EXTENSOR |
| 497: | 03C6 | 78 | LOOP214 | MOV | A,B |
| 498: | 03C7 | 95 | | SUB | L |
| 499: | 03C8 | F2D403 | | JP | LOOP223 |
| 500: | 03CB | 78 | | MOV | A,B |
| 501: | 03CC | C640 | | ADI | 40H |
| 502: | 03CE | D390 | | OUT | HAND |
| 503: | 03D0 | 3E00 | | MVI | A,0 |
| 504: | 03D2 | D3B0 | | OUT | EXTENSOR |
| 505: | 03D4 | 3E00 | LOOP223 | MVI | A,0 ; DELAY |
| 506: | 03D6 | C601 | LOOP224 | ADI | 1 |
| 507: | 03D8 | C2D603 | | JNZ | LOOP224 |
| 508: | 03DB | C39402 | | JMP | LOOP12 |
| 509: | | | | | |
| 510: | | | | | |
| 511: | | | ;100 MICRO-SECOND DELAY FOR A,D CONVERTER | | |
| 512: | | | | | |
| 513: | | | DELAY100: | | |
| 514: | 03DE | F5 | | PUSH | PSW |
| 515: | 03DF | C5 | | PUSH | B |
| 516: | 03E0 | 010000 | | LXI | B,0 |
| 517: | | | L100; | | |
| 518: | 03E3 | 0B | | DCX | B |
| 519: | 03E4 | 78 | | MOV | A,B |
| 520: | 03E5 | B1 | | ORA | C |
| 521: | 03E6 | C2E303 | | JNZ | L100 |
| 522: | 03E9 | C1 | | POP | B |
| 523: | 03EA | F1 | | POP | PSW |
| 524: | 03EB | C9 | | RET | |
| 525: | | | | | |
| 526: | | | | | |
| 527: | 03EC | | | END | START; |

What is claimed is:

1. Hand control apparatus for a quadriplegic person comprising:

a control sensor for sensing movement of a non-paralyzed part of the body of said person and generating a corresponding hand control signal, indicating means for indicating a reference value of said hand control signal, microprocessor means connected to said control sensor and programmed for generating hand closing commands and hand opening commends in accordance with the value of said hand control signal relative to said reference value, first stimulation means responsive to said hand closing commands for stimulating contraction of muscles connected for closing a hand of said person, second stimulation means responsive to said hand opening signals for stimulating contraction of muscles connected for opening said hand, and feedback means for sensing movement of said hand and transmitted a feedback signal to said microprocessor in correspondence thereto;

said microprocessor being further programmed for generating said hand closing commands in correspondence with the difference between said hand control signal and said feedback signal.

2. Apparatus according to claim 1 wherein said control sensor is a sensor for sensing movement of that shoulder of said person which is opposite said hand.

3. Apparatus according to claim 2 wherein said control sensor comprises a linear potentiometer.

4. Apparatus according to claim 1 wherein said first and second stimulation means each comprise means for generating muscle stimulating signals and surface electrodes for applying said muscle stimulating signals to said muscles.

5. Apparatus according to claim 4 wherein said surface electrodes are mounted in a cuff fitted for wearing on the forearm of said person above said hand.

6. Apparatus according to claim 4 and further comprising adjustable limit means for limiting the amplitude of said muscle stimulating signals to a predetermined maximum value.

7. Apparatus according to claim 6 and further comprising adjustable threshold means for adjusting said stimulating signals to a level at which predetermined values of said hand closing commands and said hand opening commands produce threshold movement of said hand.

8. Apparatus according to claim 7 and further comprising a control panel for mounting said indicating means, said limit means and said threshold means.

9. Apparatus according to claim 8 wherein said indicating means comprises a first pushbutton.

10. Apparatus according to claim 9 wherein said control panel comprises sequence means for indicating a sequence of steps for adjusting said apparatus; said microprocessor means being programmed for controlling said sequence means and accepting operator inputs from said control panel when said first pushbutton is depressed.

11. Apparatus according to claim 10 and further comprising a second pushbutton located on said control panel in a position widely spaced apart from said first pushbutton; said microprocessor being programmed for designating operation of said first and second pushbuttons in an alternating sequence and accepting operator inputs from said control panel only when a designated one of said pushbuttons is depressed.

12. Apparatus according to claim 11 and further comprising means mounted on said control panel for selectively interrupting power to said first and second stimulation means while permitting power to be supplied to said microprocessor means.

13. Apparatus according to claim 12 and further comprising means mounted on said control panel for resetting said microprocessor.

14. Apparatus according to claim 1 wherein said feedback means comprises pressure sensing means.

15. Apparatus according to claim 1 wherein said feedback means comprises length sensing means.

16. Apparatus according to claim 1 wherein said feedback means comprises pressure sensing means and length sensing means for alternate use in generating said feedback signal.

17. Apparatus according to claim 16 wherein said feedback means are mounted on a glove fitted for wearing on said hand.

18. Hand control apparatus for a quadriplegic person comprising:

a control sensor for sensing movement of a non-paralyzed part of the body of said person and generating a corresponding hand control signal, feedback means for sensing movement of a hand of said person and generating a corresponding feedback signal, microprocessor means for generating hand closing commands in response to said hand control signal and said feedback signal, and stimulation means responsive to said hand closing commands for stimulating contraction of muscles connected for closing said hand.

19. Apparatus according to claim 18 wherein said control sensor senses movement of a shoulder of said person.

20. Apparatus according to claim 19 wherein said shoulder is opposite said hand.

21. Apparatus according to claim 18 wherein said microprocessor generates hand opening commands; said apparatus further comprising stimulation means responsive to said hand opening commands for stimulating contraction of muscles connected for opening said hand.

22. Apparatus according to claim 21 wherein said feedback means comprises length sensing means and pressure sensing means.

23. Apparatus according to claim 18 wherein said feedback means comprises length sensing means.

24. Method of controlling closure of a paralyzed human hand comprising the steps of:

sensing movement of a non-paralyzed part of the body of the person whose hand is paralyzed, communicating to a microprocessor an indication of the movement which is so sensed, sensing closure of said hand, communicating to said microprocessor an indication of the closure which is so sensed, causing said microprocessor to generate closure commands in response to both of said indications, stimulating contraction of muscles connected for producing closure of said hand in response to said closure commands, and terminating said stimulating step when a predetermined closure of said hand has been sensed.

25. Method according to claim 24 wherein said stimulating step comprises the sub steps of:

placing a plurality of electrodes on the skin of said person in positions for stimulating said contraction, generating electrical stimulation signals corresponding to said closure commands, and
applying said electrical stimulation signals to said electrodes.

26. Method according to claim 25 and further comprising the preliminary steps of:
setting a gain for said electrical stimulation signals such that a predetermined threshold closure command produces threshold contraction of said muscles, and
setting a maximum value for said closure commands as that value which for said gain produces a predetermined maximum tolerable amount of discomfort for said person.

* * * * *

UNITED STATES PATENT AND TRADEMARK OFFICE
CERTIFICATE OF CORRECTION

PATENT NO. : 4,558,704
DATED : December 17, 1985
INVENTOR(S) : Jerrold S. Petrofsky It is certified that error appears in the above-identified patent and that said Letters Patent is hereby corrected as shown below:

Col. 8, line 27, "370a    10Kμ" should be --370a    10KΩ--.

Col. 8, line 44, "400    100KHz oscillator" should be --400    10KHz oscillator--.

Col. 12, line 3, "taken" should be --been--.

Col. 17, No. 196, "HAND IKL" should be --HAND INL--.

Col. 17, No. 238, "E62C" should be --E620--.

Col. 21, No. 348, "2" should be --20--.

Col. 23, No. 432, "034B" should be --034E--.

Col. 25, No. 467, "SUI" should be --JM--.

Col. 25, No. 470, "E,A" should be --B,A--.

Col. 27, line 18, "transmitted" should be --transmitting--.

Signed and Sealed this

Twenty-second Day of April 1986

[SEAL]

Attest:

DONALD J. QUIGG

Attesting Officer    Commissioner of Patents and Trademarks